(12) United States Patent
Robert

(10) Patent No.: US 8,263,395 B2
(45) Date of Patent: Sep. 11, 2012

(54) RECOMBINANT ADENOVIRUSES PREPARATION AND ADENOVIRUS BANKS

(75) Inventor: Jean-Jacques Robert, Sceaux (FR)

(73) Assignee: Aventis Pharma S.A., Antony (FR)

( * ) Notice: Subject to any disclaimer, the term of this patent is extended or adjusted under 35 U.S.C. 154(b) by 605 days.

(21) Appl. No.: 12/329,772

(22) Filed: Dec. 8, 2008

(65) Prior Publication Data

US 2009/0149349 A1    Jun. 11, 2009

Related U.S. Application Data

(63) Continuation of application No. 10/110,096, filed as application No. PCT/FR00/02774 on Oct. 5, 2000, now abandoned.

(60) Provisional application No. 60/168,356, filed on Dec. 1, 1999.

(30) Foreign Application Priority Data

Oct. 7, 1999   (FR) ...................................... 99 12521

(51) Int. Cl.
   *C12N 15/00*   (2006.01)
(52) U.S. Cl. ....................... 435/320.1; 435/489; 435/239
(58) Field of Classification Search ........................ None
    See application file for complete search history.

(56) References Cited

U.S. PATENT DOCUMENTS

| | | | |
|---|---|---|---|
| 5,744,133 A | 4/1998 | Lathe et al. | |
| 5,866,551 A | 2/1999 | Benoit et al. | |
| 5,888,732 A | 3/1999 | Hartley et al. | |
| 5,922,576 A * | 7/1999 | He et al. | 435/91.41 |
| 6,007,806 A | 12/1999 | Lathe et al. | |
| 6,040,174 A | 3/2000 | Imler et al. | |
| 6,133,028 A | 10/2000 | Imler et al. | |
| 6,200,798 B1 | 3/2001 | Yeh et al. | |
| 6,261,807 B1 | 7/2001 | Crouzet et al. | |
| 6,312,946 B1 | 11/2001 | Yeh et al. | |
| 6,410,298 B1 | 6/2002 | Crouzet et al. | |
| 6,426,216 B1 | 7/2002 | Perricaudet | |
| 6,630,322 B1 | 10/2003 | Perricaudet et al. | |
| 2001/0049136 A1 | 12/2001 | Imler et al. | |
| 2002/0031499 A1 | 3/2002 | Haddada et al. | |
| 2003/0004091 A1 | 1/2003 | Perricaudet et al. | |
| 2003/0096787 A1 | 5/2003 | Perricaudet et al. | |

FOREIGN PATENT DOCUMENTS

| | | |
|---|---|---|
| AU | 721654 | 6/1998 |
| EP | 0259212 | 8/1897 |
| EP | 0140308 | 5/1985 |

(Continued)

OTHER PUBLICATIONS

Volkert et al., Virology 1983 vol. 125, pp. 175-193.*

(Continued)

*Primary Examiner* — Mary E Mosher
*Assistant Examiner* — Myron Hill
(74) *Attorney, Agent, or Firm* — Lathrop & Gage LLP; James H. Velema, Esq.

(57) ABSTRACT

The invention concerns compositions and methods for preparing recombinant adenoviruses. The resulting adenoviruses can be used for transferring and/or expressing genes in cells, in vitro, ex vivo or in vivo, or also in functional genomics. More particularly, the invention concerns in particular efficient methods for producing adenovirus banks and the use of said banks in functional genomics. The invention also concerns plasmids used for constructing said adenoviruses.

17 Claims, 11 Drawing Sheets

FOREIGN PATENT DOCUMENTS

| | | |
|---|---|---|
| EP | 0185573 | 11/1985 |
| FR | 2718150 | 3/1994 |
| FR | 2730411 | 2/1995 |
| FR | 2730504 | 3/1997 |
| FR | 2755975 | 5/1999 |
| WO | WO 93/19191 | 9/1993 |
| WO | WO 94/12649 | 6/1994 |
| WO | WO 94/25073 | 11/1994 |
| WO | WO 94/26914 | 11/1994 |
| WO | WO 94/26938 | 12/1994 |
| WO | WO 94/28152 | 12/1994 |
| WO | WO 95/02697 | 1/1995 |
| WO | WO 95/27071 | 10/1995 |
| WO | WO 95/34671 | 12/1995 |
| WO | WO 96/10088 | 4/1996 |
| WO | WO 96/13596 | 5/1996 |
| WO | WO 97/47757 | 12/1997 |
| WO | WO 99/25861 | 5/1999 |

OTHER PUBLICATIONS

U.S. Appl. No. 08/718,482, filed Oct. 9, 1996, Abitol et al.

A. Tramontano et al., The Making of the Minibody: an Engineered Beta-Protein for the Display of Conformationally Constrained Peptides. Journ. of Molecular Regonition, vol. 7, 1994, pp. 9-24.

A.G. Leniche et al., Amino Acid Sequence Homology between Piv, an Essential Protein in Site-Specific DNA Inversion in Moraxella lacunata, and Transposases of an Unusual Family of insertion Elements, J. of Bacteriology, vol. 176, No. 13, Jul. 1994, pp. 4160-4164.

Andrew J. Bett et al., An efficient and flexible system for construction of adenovirus vectors with insertions or deletions in early regions 1 and 3, Proc. Natl. Acad. Sci. USA, vol. 91, Sep. 1994, pp. 8802-8806.

C. Chartier et al., Efficient Generation of Recombinant Adenovirus Vectors by Homologous Recombination in *Escherichla coli*, Journ. of Virology, vol. 70, No. 7, Jul. 1996, pp. 4805-4810.

C. M. Hamilton et al., New Method for Generating Deletions and Gene Replacements in *Escherichia coli*, Journ. of Bacteriology, vol. 171. No. 9, Sep. 1989, pp. 4617-4622.

C.W. Beard et al., Transcription Mapping of Mouse Adenovirus Type 1 Early Region 3, Virology, vol. 175, 1990, pp. 81-90.

D. Hanahan, Studies on Transformation of *Escherichia coli* with Plasmids, J. Mol. Biol. vol. 166, 1983, pp. 557-580.

D.A. Simoes et al., A Sugar-Inducible Excretion System for the Production of Recombinant Proteins with *Escherichia coli*, Ann. of New York Acad. of Sci., vol. 646, 1991, pp. 254-258.

D.T. Dang et al., Use of Yeast Site-Specific Recombinase to Generate Embryonic Mosaics in *Drosophila*, Development Genetics, vol. 13, No. 5, pp. 367-375.

F. Bolivar et al., Construction and Characterization of New Cloning Vehicles II. A Multipurpose Cloning System, Gene, vol. 2, 1997, pp. 95-113.

F. Heffron et al., Deletions Affecting the Transposition of an Antibiotic Resistance Gene, Genetics, vol. 74, No. 2, Feb. 1977, pp. 702-706.

F. Rossi et al., Monitoring Protein-Protein Interactions in Intact Eukaryotic Cells by Beta-galactosidase Complementation, Proc. Natl. Acad. Sci, USA, vol. 94, Aug. 1997, pp. 8405-8410.

F.L. Graham et al., Characteristics of a Human Cell Line Transformed by DNA from Human Adenovirus Type 5, J. Gen. Virol. vol. 36, 1977, pp. 59-72.

F.L. Graham, Covalently Closed Circles of Human Adenovirus DNA are Infectious, The EMBO Journal, vol. 3, No. 12, 1984, pp. 2917-2922.

G. Ditta et al., Plasmids Related to the Broad Host Range Vector, pRK290, Useful for Gene Cloning and for Monitoring Gene Expression, Plasmid, vol. 13, 1985, pp. 149-153.

G. Ghosh-Choudhury et al., Human Adenovirus Cloning Vectors Based on Infectious Bacterial Plasmids, Gene, vol. 50, 1986, pp. 161-171.

G. Riced. Goeddel, Random PCR Mutagenesis Screening of Secreted Proteins by Direct Expression in Mammalian Cells, Proc. Natl. Acad Sci. USA, vol. 89, Jun. 1992, pp. 5467-5471.

H.A. Jaffe et al., Adenovirus-mediated in vivo gene transfer and expression in normal rat liver, Nature Genetics vol. 1, Aug. 1992, pp. 372-378.

H.J. Kwon et al., Flexibility in DNA Recombination: Structure of the Lambda integrase Catalytic Core, Science, vol. 276, Apr. 4, 1997, pp. 126-131.

J. Crouzet et al., Recombination construction in *Escherichia coli* of infectious adenoviral genomes, Proc. Natl. Acad. Sci. USA, vol. 94, Feb. 1997, pp. 1414-1419.

J. Vieira et al., The pUC Plasmids, an M13mp7-derived System for Insertion Mutagenesis and Sequencing With Synthetic Universal Primers, Gene, vol. 19, 1982, pp. 259-268.

M. Dagert et al., Prolonged Incubation in Calcium Chloride Improves the Competence of *Escherichia coli* Cells, Gene, vol. 6, 1979, pp. 23-28.

M. Levrero et al., Defective and Nondefective Adenovirus Vectors for Expressing Foreign Genes In Vitro and In Vivo, Gene, vol. 101, 1991, pp. 195-202.

N.D. Sinha et al., Polymer Support Oligonucleotide synthesis XVII1. 2: Use of Beta-cyanoethyl-Ni, N-dialkylamino-/N-morpholino, Nucleic Acids Research, vol. 12, No. 11, 1984, pp. 4539-4557.

P. Colas et al., Genetic Selection of Peptide Aptamers That Recognize and Inhibit Cyclin-Dependent Kinase 2, Nature, vol. 380, Apr. 11, 1996, pp. 548-550.

P.A. Patten et al., Applications of DNA Shuffling to Pharmaceuticals and Vaccines, Current Opinion in Biotech. vol. 8, 1997, pp. 724-733.

R. Wirth et al., Transformation of Various Species of Gram-Negative Bacteria Belonging to 11 Different Genera by Electroporation, Mol. Gen. Genet, vol. 216, 1989, pp. 175-177.

S. Akli et al., Transfer of a foreign gene into the brain using adenovirus vectors, Nature Genetics, vol. 3, Mar. 1993, pp. 224-228.

S. Slater et al., Simple Phagemid-Based System for Generating Allele Replacements in *Escherichia coli*, Journ. of Bacteriology, vol. 175, No. 13, Jul. 1993, pp. 4260-4262.

T. He et al., A simplified system for generating recombinant adenoviruses, Proc. Natl. Acad. Sci. USA, vol. 95, Mar. 1998, pp. 2509-2514.

T. Ragot at al., Efficient Adenovirus-Mediated Transfer of a Human Minidystrophin Gene to Skeletal Muscle of mdx Mice, Nature, vol. 361, Feb. 18, 1993, pp. 647-650.

V.L. Miller et al., A Novel Suicide Vector and Its Use in Construction of Insertion Mutations: Osmoregulation of Outer Membrance Proteins and Virullence Determinants in Vibrio cholerae Requires toxR, Journ. of Bacterioiogy, vol. 170, No. 6, Jun. 1988, pp. 2575-2583.

W. Baubonis et al., Genomic targeting with purified Cre recombinase, Nucleic Acids Research, vol. 21, No. 9, 1993, pp. 2025-2029.

\* cited by examiner

RECOMBINANT ADENOVIRUSES PREPARATION AND ADENOVIRUS BANKS

The present invention relates to compositions and methods for preparing recombinant adenoviruses. The adenoviruses which are produced can be used for transferring genes into, and/or expressing genes in cells, in vitro, ex vivo or in vivo, or in functional genomics as well. In particular, the present invention relates to methods which are particularly efficacious for producing adenoviral libraries and to the use of these libraries in functional genomics. The invention also relates to plasmids which are used for constructing these adenoviruses, to cells which harbor these plasmids and to kits which comprise these plasmids, cells and/or adenoviral libraries.

The adenoviruses exhibit certain properties which are advantageous for transferring genes into, and/or expressing genes in cells. In particular, they have a relatively broad host spectrum, are able to infect quiescent cells, have substantial cloning capacity and do not integrate into the genome of the infected cell. In addition, they have not to date been associated with any significant pathologies in man and have therefore been used for transferring genes of interest, in vitro or in vivo, into various human tissues such as muscle (Ragot et al., Nature 361 (1993) 647), liver (Jaffe et al., Nature genetics 1 (1992) 372), the nervous system (Akli et al., Nature genetics 3 (1993) 224), tumors, smooth muscle, etc. These same properties make the adenoviral vector a tool of choice for exploiting the findings derived from genomics.

Functional genomics is understood as being the area of science which is concerned with exploiting genomes or the findings from the genomes of various organisms for the purpose of expressing them in functional terms. In view of their properties, adenoviral vectors which carry an exogenous sequence can be used for determining the function of this sequence in a variety of experimental models. In particular, adenoviral vectors can be used to study a therapeutic target (in the sense or is understood in the pharmaceutical industry) in a cell model in vitro or in vivo in an animal. When this sequence is known and characterized, adenoviral vectors can be used for functionally validating this target. More widely, in the context termed functional genomics, the adenoviral gene transfer vector could represent a powerful tool for identifying the function of a nucleic acid sequence in an experimental eukaryotic model without previously having any particular information on the nature or function of this sequence, including situations in which a large number of sequences have to be studied on mass.

However, the industrial and therapeutic exploitation of adenoviruses, or their exploitation in functional genomics, is still limited, in particular by the current methods of preparing these recombinant viruses. In particular, the methods which are currently available do not enable adenovirus populations incorporating heterologous nucleic acids to be produced simply, rapidly and clonally, especially when large numbers of heterologous nucleic acids have to be studied, as is the case in functional genomics. The present invention specifically provides a solution to these problems. Thus, the present invention describes novel tools and novel methods for constructing recombinant adenoviruses. In particular, the invention describes genetic constructs (plasmids), cells and protocols which enable high-quality adenoviruses to be produced rapidly. More specifically, the invention makes it possible to prepare adenoviral libraries which comprise a high number of heterologous nucleic acids.

Figure 1:
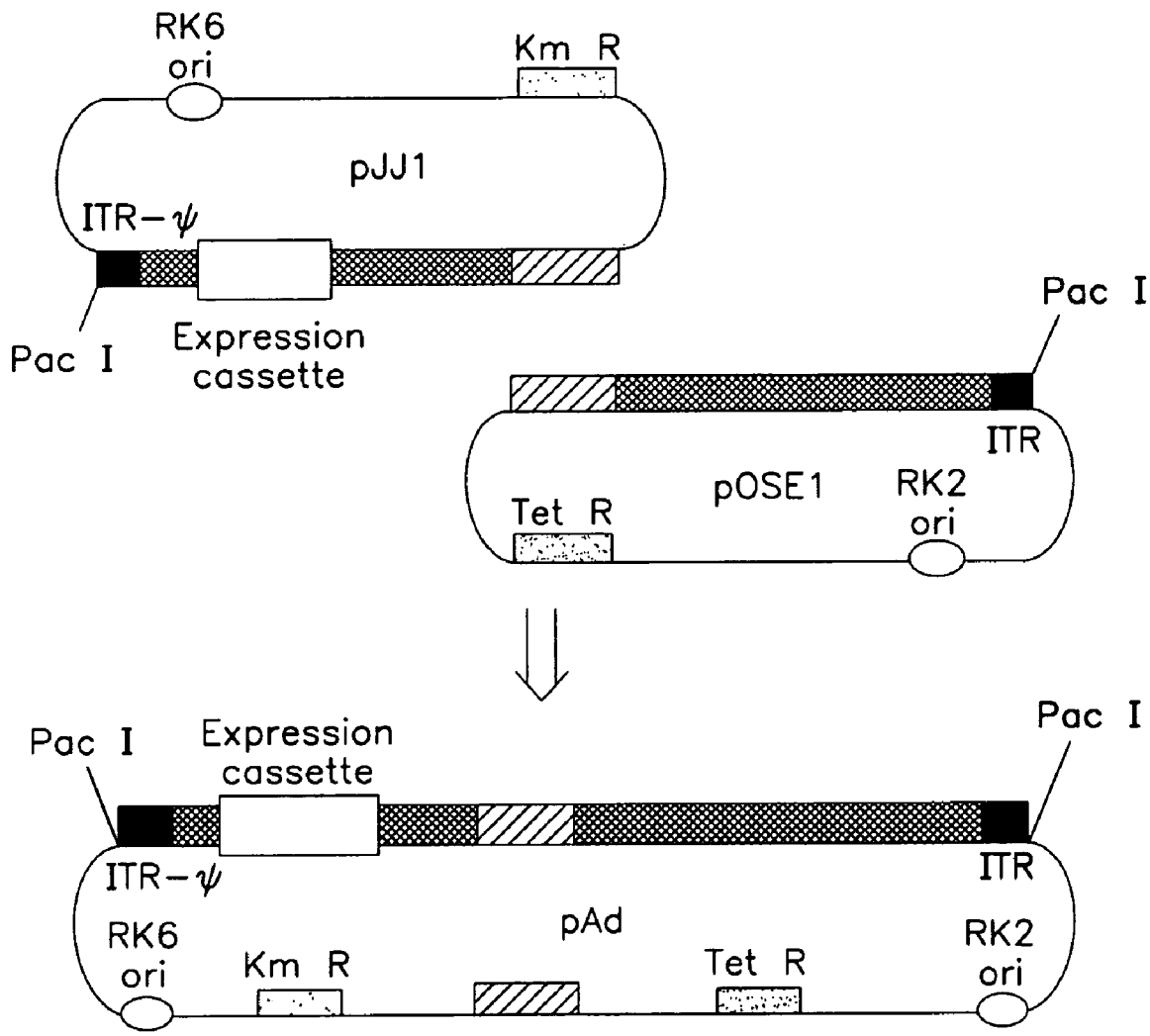
FIG. 1 Diagram of the principle of the invention. A shuttle plasmid pJJ1 and a parental plasmid pOSE1, each of which possesses a complementary fragment, form a coaggregate by means of homologous recombination in E. coli, thereby generating a complete recombinant adenovirus genome which carries an exogenous sequence.
KmR: gene for resistance to kanamycin. Tet R: gene for resistance to tetracycline. RK2 Ori: origin of replication from plasmid RK2. RK6 Ori: origin of replication from plasmid RK6

One aspect of the present invention therefore resides in the use of recombinant adenoviruses for determining the biological function of a nucleic acid or a protein.

Another aspect of the invention resides in the use of adenoviruses for constructing expression libraries for the purpose of analyzing nucleic acids of unknown function and/or structure.

The invention also relates to adenoviral expression libraries, that is adenovirus populations which comprise nucleic acid inserts which derive from any DNA library.

The invention also relates to methods and tools for producing these adenoviruses, in particular these libraries, in particular, and advantageously, simultaneously constructing recombinant adenoviruses from nucleic acid libraries.

Adenoviruses are linear, double-stranded DNA viruses having a size of approximately 36 kb. Their genome comprises, in particular, an inverted repeat sequence (ITR) at each end, an encapsidation sequence (Psi), early genes and late genes. The main early genes are contained in the E1, E2, E3 and E4 regions. Of these, the genes contained in the E1 region are required for propagation of the virus. The E4 region is also important in regulating replication of the adenoviral genome. The main late genes are contained in the L1 to L5 regions. The genome of the adenovirus Ad5 has been completely sequenced and is accessible in databases (see, in particular, Genbank M73260). Similarly, parts, if not the whole, of other human or animal adenoviral genomes (Ad2, Ad7, Ad12, CAV-2, etc.) have also been sequenced.

Furthermore, as pointed out above, adenoviruses have already been used for transferring genes in vivo. To this end, different adenovirus-derived vectors have been prepared which incorporate a variety of genes (β-gal, OTC, α-1AT, cytokines, enzymes, growth factors, etc.). In each of these constructs, the genome of the adenovirus has been modified so as to make it incapable of autonomously replicating and/or propagating following gene transfer. Thus, the constructs which are described in the prior art are adenoviruses from which one or more regions selected from E1, E2, E3, E4, pIX, Iva2, etc. have been deleted. Particular constructs lack the E1 region, the E1 and E3 regions, the E1 and E4 regions, the E1, E4 and E3 regions, or all the coding regions of the adenovirus (gutless vector), for example. These vectors generally contain a heterologous nucleic acid which it is desired to transfer into cells or to study. This nucleic acid can be inserted into different sites in the recombinant genome, either while at the same time replacing deleted regions or into other locations. Examples of adenoviral vectors are described, in particular, in Levrero et al., Gene 101 (1991) 195; Gosh-Choudhury et al., Gene 50 (1986) 161, WO94/12649, WO94/28152, WO94/28938, WO95/34671, WO96/10088, WO95/02697, WO95/27071, etc., which publications are hereby incorporated by reference.

The recombinant adenoviruses are produced by transfecting the DNA of the recombinant virus into a competent encapsidating cell line. The transfection can be a single transfection, when a construct carrying the whole of the genome of the recombinant virus is available, or, as is more often than not the case, a cotransfection of several DNA fragments which supply the different parts of the recombinant viral genome. In this case, the process involves one or more steps of homologous recombination between the different constructs being carried out in the encapsidating cell line in order to generate the DNA of the recombinant virus. In order to implement one or other of these methods, it is therefore necessary to have available appropriate constructs which carry all or parts of the genome of the recombinant adenovirus which it is desired to produce.

The prior art describes a variety of methods for preparing these constructs in vitro. The most generally employed technique consists in isolating the viral DNA and then using the conventional methods of molecular biology (digestion, ligation, etc.) to modify it in vitro. The resulting constructs are then purified and used for transfecting the encapsidating cell lines. However, this technique involves producing stocks of virus and purifying viral DNA for each construct or for each manipulation of the DNA of the recombinant virus and is not therefore suitable for producing different stocks or libraries. In order to remedy these drawbacks, it has been suggested that prokaryotic plasmids be employed for preparing the viral DNAs which can be used for the transfection. In particular, Bett at al. (PNAS 91 (1994) 8802) describes constructing a plasmid which replicates in E. coli and which contains a modified adenoviral genome (plasmid pBHG10). More precisely, this plasmid carries an adenoviral genome which is deleted for the E1, E3 and Psi regions, which has been circularized by the ITR sequences being linked together and which comprises a part of plasmid pBR322, which is inserted within the 188-1339 region of the genome of the adenovirus. While this plasmid can be replicated in E. coli and manipulated for inserting genes of interest, it still suffers from disadvantages. Its use for producing viruses involves, in particular, linearizing the contiguous ITRs and carrying out a recombination which, on account of the constructs, leads to regions derived from the prokaryotic plasmid being incorporated into the recombinant adenoviral genome. Other plasmids which are of this same type and which suffer from the same kinds of disadvantage have been described for example, by Graham (EMBO J. 3(12) (1984) 2917). New methods which are based, in particular, on the homologous recombination of two plasmids, and which use yeast artificial chromosomes (YACs, Ketner et al., 1994) or bacteria (Chartier et al., 1996, Crouzet et al., 1997, He at al., 1998) have been described more recently. Although more effective than the previous ones, these methods are more complex. The YAC system makes it necessary to culture and manipulate yeasts (Ketner et al., 1994). The E. coli systems involve several successive steps (some of which, i.e. electrotransformation and sucrose selection, are critical). It will be noted, in particular, that, in all cases, one or more steps of screening clones are required for selecting a final clonal recombinant vector carrying an infectious adenoviral genome. Even if these methods enable stocks of an adenovirus carrying a given therapeutic gene to be produced effectively and clonally, it is not, however, possible to use them satisfactorily for producing recombinant adenoviruses at a high output rate, in particular for simultaneously producing a large number of recombinant adenoviruses incorporating different nucleic acids.

The complexity and number of the operations which are required for producing these viruses therefore put a brake on using the adenoviral vector as a system for gene transfer or analysis. There is therefore a clear need in the prior art to have available appropriate plasmids, which are easy to manipulate and amplify in vitro, for preparing recombinant adenoviral genomes. It is also important that the genomes which are produced in this way should be virtually devoid of regions which are derived from the plasmid and which are capable (i) of inducing an immune response (ii) of encoding resistance proteins and (iii) of reducing the capacity of the virus as a vector. There is also a need for methodologies which enable recombinant adenoviruses to be more easily generated clonally, rapidly and in large numbers.

The present invention makes it possible, in particular, to remedy these drawbacks. Thus, the present invention describes novel compositions and methods for producing recombinant adenoviruses which meet these criteria. In particular, the compositions and methods of the invention enable recombinant adenoviruses, which can be used therapeutically or for searching for pharmaceutical targets, to be produced clonally, rapidly and efficiently at a high output rate.

The present invention is based, in particular, on using two plasmids (in particularly prokaryotic plasmids) which are able to generate, in one homologous recombination step in a host cell (in particular a prokaryotic cell), a plasmid which comprises a complete adenoviral genome which can easily be excised for producing recombinant adenoviruses.

In a general manner, therefore, the process of the invention comprises:

Constructing, in a first step, a first plasmid (termed "shuttle" plasmid), preferably a prokaryotic plasmid, which comprises a first truncated recombinant adenoviral genome which comprises at least one heterologous nucleic acid (cloning step). The first truncated genome preferably comprises an ITR, a heterologous nucleic acid, a region of adenoviral homology and, where appropriate, an encapsidation sequence.

This first plasmid is brought into contact, in a second step, with a second plasmid (termed "parent" plasmid) which comprises a second truncated recombinant adenoviral genome which is complementary to the first genome, making it possible, by means of homologous recombination, to produce a final plasmid which comprises a complete recombinant adenoviral genome (recombination step). The second truncated adenoviral genome preferably comprises at least one ITR, a region of adenoviral homology which is identical to that present in the first genome, and an encapsidation sequence (if the latter is not present in the first genome). This second truncated adenoviral genome can furthermore also comprise another nucleic acid of interest.

In a third step, the complete recombinant adenoviral genome is excised from the final plasmid and introduced into an encapsidating cell line in order to produce the recombinant adenoviruses which incorporate the complete the recombinant adenoviral genome (step of producing adenoviruses).

In a fourth, optional step, the recombinant adenoviruses are used for infecting:

a biological material comprising cells, for the purpose of analyzing the properties of the nucleic acid (functional analysis step).

a cell culture in vitro or ex vivo, for the purpose of producing a protein, polypeptide or peptide which is encoded by the heterologous nucleic acid, a cell, tissue, organ or organism, for the purpose of producing in vivo a protein, polypeptide or peptide which is encoded by the heterologous nucleic acid.

The present invention thus makes it possible to obtain, in one (homologous recombination) step, a prokaryotic plasmid which carries a (complete) functional adenoviral genome which can be excised with one or more appropriate enzymes. This final plasmid thus results from integrating a first (shuttle) plasmid, which carries adenoviral sequences (at the very least an ITR sequence and an encapsidation sequence) and which is provided with a heterologous nucleic acid of interest, into a second (parent) plasmid, which carries complementary adenoviral sequences (at the very least a second ITR sequence), by means of a homologous recombination event which takes place via a sequence which is common to the two plasmids (sequence of adenoviral homology). This homologous recombination event gives rise, via this coaggregate, to a functional adenoviral genome.

One of the advantages of the process of the invention is its simplicity, which enables it to be carried out in parallel using a large number of shuttle plasmids. Thus, the first step of the process advantageously comprises cloning a library of nucleic acids into the shuttle plasmids, thereby generating a library of final plasmids which are carrying a functional adenoviral genome and whose structure is identical apart from the inserts which they contain. This cloning step is preferably carried out while keeping each clone separate, for example in a microtitration plate well. Furthermore, this step can be automated. The resulting shuttle plasmid library is then used in the recombination step, with each shuttle plasmid in the library being brought into contact with the parent plasmid. This process thus leads, in parallel and simultaneously, to the production of large numbers of recombinant adenoviruses containing a heterologous nucleic acid (i.e. an adenoviral expression library). This library can then be tested on the biological material (step 4) in order to identify clones which exhibit a sought-after biological activity.

The invention can be used with any type of adenovirus and prokaryotic cell and can be based on different nucleic acid libraries, as will be illustrated in detail in the text which follows.

Definitions

Recombinant adenovirus: the term recombinant adenovirus refers, within the meaning of the invention, to any adenovirus whose genome has been modified by deleting and/or inserting and/or substituting bases. A recombinant adenovirus is therefore, more specifically, an adenoviral particle which is generally infectious and which comprises a recombinant adenoviral genome. Depending on the modification(s) which has/have been made to the genome, the recombinant virus may be defective for replication, that is incapable of replicating and/or propagating autonomously in a cell. The recombinant adenovirus can be prepared from any adenovirus serotype, in particular human (for example type C adenoviruses such as Ad5, Ad2, Ad7, Ad12, etc.) or animal (such as canine adenoviruses, for example CAV-2) adenoviruses.

Adenoviral genome: the term "adenoviral genome" refers to the DNA molecule which is present in an adenovirus or its sequence or a copy or replica of it. A recombinant adenoviral genome is a nucleic acid whose sequence corresponds to the sequence of an adenovirus genome and comprises one or more modifications. The modifications comprise, for example, deletions (for example of all or part of the E1, E2, E3, E4, etc. regions), insertions (such as, for example of one or more heterologous nucleic acids) or changes in codon usage.

The recombinant adenoviral genome which is generated by the compositions and methods of the invention is advantageously a "complete" or "functional" genome, that is a genome which does not require other regions to be supplied by recombination or ligation in order to produce viral stocks in the selected encapsidating cell lines. Such a "complete" genome therefore advantageously comprises at least one encapsidation sequence and a heterologous nucleic acid, with the encapsidation sequence and the heterologous nucleic acid together being flanked by an ITR sequence at each end. Another advantageous feature of the plasmids according to the invention derives from the fact that the complete recombinant adenoviral genome which is obtained is not interrupted by regions of the prokaryotic plasmid. For this reason, the genomes which are produced essentially do not contain regions of the plasmid, the disadvantages of which have been mentioned above. Furthermore, in the plasmids according to the invention, the ITRs of the adenoviral genome are not contiguous, thereby making it possible to obtain complete linear recombinant viral genomes which can be used directly for producing the recombinant viruses.

The recombinant adenoviral genome preferably comprises at least ITR sequences and a sequence for encapsidation. The inverted repeat sequences (ITRs) constitute the origin of replication of the adenoviruses. They are located at the ends of the viral genome, from which they can be easily isolated using conventional molecular biological techniques known to the skilled person. The nucleotide sequence of the ITR sequences of human adenoviruses (in particular of serotypes Ad2 and Ad5) is described in the literature as are those of canine adenoviruses (in particular CAV1 and CAV2). For example, in the Ad5 adenovirus, the left-hand ITR sequence corresponds to the region comprising nucleotides 1 to 103 of the genome.

The encapsidation sequence (also referred to as the Psi sequence) is required for encapsidating the viral genome. In the genome of wild-type adenoviruses, it is located between the left-hand ITR and the E1 region. It can be isolated or synthesized artificially using conventional molecular biological techniques. The nucleotide sequence of the encapsidation sequence of human adenoviruses (in particular of serotypes Ad2 and Ad5) is described in the literature, as is that of canine adenoviruses (in particular CAV1 and CAV2). For example, in the Ad5 adenovirus, a functional encapsidation sequence is present between nucleotides 194 and 358 of the genome.

In one preferred embodiment of the invention, the genome of the adenovirus lacks all or part of the E1 region. This is because the E1 region is essential for viral replication and its inactivation leads to the formation of viruses which are defective for replication, that is unable to replicate autonomously following gene transfer in vivo. The E1 region, or any other viral region under consideration, can be rendered nonfunctional using any technique known to the skilled person, in particular by means of total deletion, substitution, partial deletion or the addition of one or more bases in the gene(s) under consideration. Such modifications can easily be carried out directly on the plasmids of the invention, for example, by means of genetic engineering techniques. Advantageously, the genome of the adenovirus which is generated lacks a part of the E1 region between nucleotides 454 to 3328 (PvuII/BglII fragment) or 382 to 3446 (HinfII-Sau3A fragment).

A truncated recombinant adenoviral genome refers to a DNA which corresponds to the sequence of a terminal part of an adenoviral genome, that is from one end (ITR). Two truncated recombinant genomes are said to be complementary when they each carry a complementary part of an adenoviral genome and when they can reconstitute a complete recombinant adenoviral genome by means of homologous recombination.

Heterologous nucleic acid: the term "heterologous nucleic acid" refers to any nucleic acid which is inserted into the recombinant adenoviral genome and whose transfer, expression or functional study are sought-after. A heterologous nucleic acid is essentially a nucleic acid having an origin different from an adenovirus ("heterologous"), for example which derives from a human cells or is of animal, plant, viral (other than the adenovirus used as the vector), prokaryotic, lower eukaryotic, synthetic or semi-synthetic origin. The size of the heterologous nucleic acid may vary as long as the recombinant adenoviral genome which contains it does not exceed the maximum size which enables it to be encapsidated in an adenoviral particle (less than 40 kb in all). Thus, the heterologous nucleic acid can be a nucleic acid having a length greater than 30 kb when sufficient regions of the adenovirus have been deleted. In this regard, the nucleic acid can comprise a region encoding a given protein, polypeptide or peptide, for example a cDNA, a gDNA or a synthetic DNA. The nucleic acid can also be of unknown structure, being derived, for example, from a clone belonging to a nucleic acid library. Furthermore, the recombinant adenoviral genome can comprise several heterologous nucleic acids which are inserted at different sites in the genome.

Description of the Plasmids

As pointed out above, the present invention requires two (prokaryotic) plasmids, i.e. the shuttle plasmid and the parent plasmid, each of which contains a complementary fragment of a recombinant adenovirus genome. At least one of these plasmids possesses a heterologous nucleic acid (or an insertion site for such a nucleic acid) which is of interest for gene therapy, for producing a recombinant protein or for a functional genomic approach, for example. Advantageously, the ends (ITR sequences) of each of the truncated genomes carried by each of the plasmids are flanked (5' in the case of the left-hand ITR and 3' in the case of the right-hand ITR) by a site which is not present in the said genome in order to enable the complete genome to be excised following recombination. These plasmids carry a truncated genome of the adenovirus and are unable individually to generate an infectious adenoviral genome. Each of these two plasmids possesses the part which is complementary to the other for generating, by means of cointegration, a final plasmid which then possesses the whole of an adenovirus genome flanked by two ITRs and by at least one restriction site which is not present in the said genome. The recombinant adenovirus genome fragment which is present in these plasmids is an incomplete genome which is not able, by itself, to prove infectious subsequently. This is particularly advantageous since only the cointegrat of the two plasmids is able to generate a functional genome.

These plasmids are depicted, for example, in FIG. 1 and are described in more detail in the text which follows. These plasmids are preferably prokaryotic plasmids and generally comprise a plasmid region and an adenoviral region. The plasmid region enables the plasmid to replicate and/or be selected in a host cell, in particular in a prokaryotic host cell. The adenoviral region (truncated genome) supplies a part of the recombinant adenoviral genome, which part, after recombination with the adenoviral region of the complementary (parent or shuttle) plasmid, reconstitutes the complete recombinant adenoviral genome.

The region which permits replication in prokaryotic cells, and which is used in the plasmids of the invention, can be any origin of replication which is functional in selected cells. It can be an origin of replication which is derived from a plasmid belonging to the P incompatibility group (example=pRK290), which permits replication in *E. coli* pol A strains. More generally, it can be any origin of replication which is derived from a plasmid which replicates in the prokaryotic cells. This plasmid can be a derivative of pBR322 (Bolivar et al., 1977), a derivative of pUC (Viera and Messing, 1982) or a derivative of other plasmids which are derived from the same incompatibility group, that is from ColE1 or pMB1, for example. These plasmids can furthermore be selected from other incompatibility groups which replicate in *Escherichia coli*. They can be plasmids which are derived from plasmids which belong to the A, B, FI, FII, FIII, FIV, H1, H11, I1, I2, J, K, L, N, OF, P, Q, T, U, W, X, Y, Z or 9 incompatibility groups, for example. Other plasmids can also be used, including plasmids which do not replicate in *E. coli* but replicate in other hosts such as *B. subtilis, Streptomyces, P. putida, P. aeruginosa, Rhizobium meliloti, Agrobacterium tumefaciens, Staphylococcus aureus, Streptomyces pristinaespiralis, Enterococcus faecium* or *Clostridium*. Preference is given to using origins of replication which are derived from plasmids which replicate in *E. coli*.

The region which permits selection of the prokaryotic cells which harbor the plasmids of the invention can consist, in particular, of any gene which confers the resistance to a product, in particular to an antibiotic. Thus, the genes which confer resistance to kanamycin (Kan$^r$), to ampicillin (Amp$^r$), to tetracycline (tet$^r$) or to spectinomycin, for example, which are commonly used in molecular biology (Maniatis et al., 1989), may be mentioned. Other genes than genes encoding markers for resistance to an antibiotic may be used for the plasmid selection. In a general manner, the gene is a gene which gives the bacterium a function which it no longer possesses (this can correspond to a gene which has been deleted from the chromosome or has been rendered inactive), with the gene on the plasmid then reestablishing this function. As an example, the gene can be a gene for a transfer RNA which reestablishes a deficient chromosomal function (Somoes et al., 1991).

The shuttle plasmid and the parent plasmid preferably carry different origins of replication and/or markers in order to enable each element to be selected.

The adenoviral region contained in each of the plasmids essentially corresponds to the sequence of a truncated adenoviral genome. These truncated genomes, which are carried by each of the plasmids, are complementary, that is able to generate a complete (and linear) recombinant adenoviral genome following homologous recombination. In addition, the truncated genomes, which are carried by each of the plasmids, are preferably flanked by one or more restriction sites which are not present in an adenoviral genome, such that the complete recombinant adenoviral genome which is produced by recombination is flanked by these sites.

Truncated Genome which is Present in the Shuttle Plasmid

As pointed out above, the shuttle plasmid is intended for receiving the nucleic acid of interest with a view to this nucleic acid being incorporated into a recombinant adenoviral genome.

The adenoviral region of the shuttle plasmid corresponds to the left-hand part or to the right-hand part of an adenoviral genome, from its end (an ITR sequence) and up to a chosen region of adenoviral homology which will enable homologous recombination to take place between the two plasmids. This adenoviral genome additionally comprises one or more genetic modifications.

In a first embodiment, the truncated genome which is present in the shuttle plasmid corresponds to the left-hand part of the final recombinant adenoviral genome. In this embodiment, the truncated genome comprises, for example, a sequence which passes from the left-hand ITR through to the region encoding the pIX (and/or Iva2) protein, with the heterologous nucleic acid being inserted in replacement of all or part of the E1 region. In this particular embodiment, the region of adenoviral homology consists of the region encoding the pIX (and/or Iva2) protein.

In another embodiment, the truncated genome which is present in the shuttle plasmid corresponds to the right-hand part of the final recombinant adenoviral genome. In this embodiment, it comprises, for example, the sequence which passes from the right-hand ITR through to the region encoding the pIX (and/or Iva2) protein, with the heterologous nucleic acid being inserted in replacement of all or part of the E4 or E3 region, for example. In this particular embodiment, the region of adenoviral homology also consists of the region encoding the pIX (and/or IVa2) protein.

Furthermore, in one particular embodiment, the region of homology consists of a modified adenoviral sequence. Thus, the region of homology can consist, for example, of a region of the adenovirus which has been modified by changing the codon usage, by utilizing the degeneracy of the genetic code. Such modifications have been described in Application WO99/25861, which is hereby incorporated by reference. In one particular embodiment, the region of adenoviral homology consists of a region which encodes the degenerate pIX (and/or Iva2) protein.

It is to be understood that the region of adenoviral homology can correspond to different regions of the genome depending on the chosen structure of the final recombinant adenoviral genome (which is generated after recombination). In fact, the adenoviral region of the parent plasmid can extend from the left-hand ITR through to the E3 region, and it is then this region which constitutes the zone of adenoviral homology. More generally, the region of adenoviral homology is a sequence which corresponds to any region of a wild-type or modified adenoviral genome which enables recombination to take place between the shuttle plasmid and the parent plasmid so as to generate the final recombinant adenoviral genome. This region of homology is therefore essentially identical in the shuttle plasmid and in the parent plasmid. It can correspond to different parts of the genome of an adenovirus depending on the type of constructs employed.

One particular embodiment of the invention resides in a shuttle plasmid which comprises a truncated genome which comprises the left-hand ITR region, the encapsidation sequence, the heterologous nucleic acid and a region of adenoviral homology which consists of a region which encodes the wild-type or degenerate pIX (and/or Iva2) protein (cf. plasmids pJJ1 and pIG5, for example).

Furthermore, in a preferred embodiment of the invention, the truncated adenoviral genome is flanked, in the direction of the ITR, by a site which is not present in the adenoviral genome, for example a PacI site.

Truncated Genome which is Present in the Parent Plasmid

As pointed out above, the parent plasmid carries a truncated adenoviral genome which is able, by means of recombination, to complete the truncated genome which is present in the shuttle plasmid. Its structure therefore depends on the structure of the shuttle plasmid. Furthermore, the parent plasmid can also contain a nucleic acid which is different from that carried by the shuttle plasmid.

Thus, when the adenoviral region of the shuttle plasmid corresponds to the left-hand part of an adenoviral genome, the truncated genome which is present in the parent plasmid corresponds to its right-hand part, extending from the ITR through to the region of adenoviral homology. Vice versa, when the adenoviral region of the shuttle plasmid corresponds to the right-hand part of an adenoviral genome, the truncated genome which is present in the parent plasmid then corresponds to its left-hand part, extending from the ITR through to the region of adenoviral homology.

In a first embodiment, the truncated genome which is present in the parent plasmid corresponds to the right-hand part of the final recombinant adenoviral genome. In this embodiment, it comprises, for example, the sequence which passes from the right-hand ITR through to the region encoding the pIX (and/or Iva2) protein. Furthermore, the genome can comprise gene modifications such as deletions of all or part of all or part of the E4 or E3 regions, for example.

In another embodiment, the truncated genome which is present in the parent plasmid corresponds to the left-hand part of the final recombinant adenoviral genome. In this embodiment, it comprises, for example, a sequence which passes from the left-hand ITR through to a sequence close to the E4 region. Furthermore, the genome can comprise gene modifications, such as deletions of all or part of all or part of the E1 region, for example.

Figure 4:
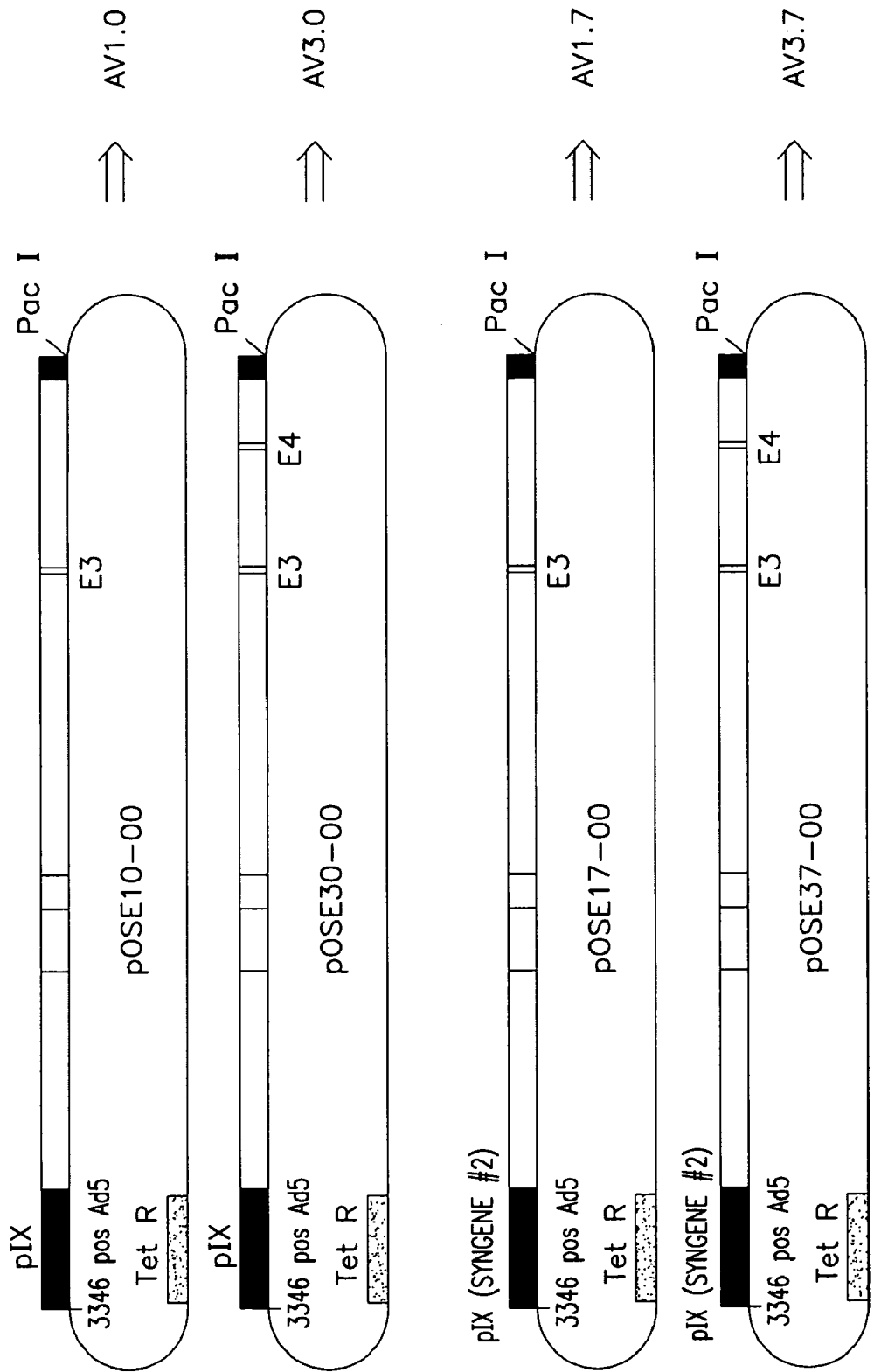
FIG. 4 Maps of different versions of parental plasmids which can be used by the invention to generate different versions of recombinant adenoviral vectors, in particular vectors which are deleted for E1 and E3 (pOSE 10-00), vectors which are deleted for E1 and E3 and provided with the pIX region in its syngen#2 form (WO99/25861) (pOSE 17-00), vectors which are deleted for E1, E3 and E4 (pOSE 30-00) and vectors which are deleted for E1, E3 and E4 and provided and provided with the pIX region in its syngen#2 form (pOSE37-00).

The parent plasmid preferably carries a truncated genome which corresponds to the right-hand part of the adenoviral genome and which contains a nonfunctional E3 region. More preferably, it contains a nonfunctional E4 region. Still more preferably, it contains a deletion of all or part of the ORF3 and/or ORF6 reading frames of the E4 region. In another particular embodiment, the parent plasmid carries a truncated genome which corresponds to the right-hand part of the adenoviral genome and includes functional E3 and E4 regions.

pOSE1, pOSE10-00, pOSE30-00, pOSE17-00 and pOSE37-00 (cf. FIGS. 1 and 4) represent specific examples of these plasmids.

In this embodiment, the shuttle plasmid carries a truncated genome which corresponds to the left-hand part of the adenoviral genome and contains a deletion of all or part of the E1 region.

Two plasmids which are particularly preferred within the meaning of the invention are the plasmid pOSE17-00 and the plasmid pIG5. pOSE17-00 (parent plasmid) comprises the origin of replication of plasmid RK2 and the gene for resistance to tetracycline, and possesses a fragment of the adenoviral genome, which begins at base 3520 of Ad5 and continues through to the right-hand ITR, which is flanked by a PacI site. This genome fragment possesses a nonfunctional E3 region and a sequence in which pIX and Iva2 have been modified, as described in Application WO99/25861. The pIG5 plasmid (shuttle plasmid) possesses an RK6 origin of replication and is unable to replicate in *E. coli* pir-strains. pIG5 possesses the ITR and encapsidation regions preceded by a PacI site, the desired expression cassette and a region which is homologous to pOSE17-00 (a sequence in which pIX and Iva2 are modified, as described in Application WO99/25861). The desired genome is thus reconstructed by homologous recombination due to the presence of the region which is homologous between the two plasmids (i.e. the sequence in which pIX and Iva2 are modified, as described in Application WO99/25861).

The process of the invention thus makes it possible to generate a complete (infectious) recombinant genome from two plasmids which each supply a part of the genome (one plasmid carrying the left-hand ITR sequence preceded by a PacI site and a set of viral or nonviral sequences and one plasmid carrying, preceded by viral or nonviral sequences, the right-hand ITR followed by a PacI site, the choice of the viral or nonviral sequences depend on the choice of the planned construct, recombinant adenovirus vector deleted for all or part of the viral genes); with the two plasmids possessing sequences in common which are sufficient for effecting homologous recombination and which exhibit an overlap in a sequence enabling the homologous recombination event to take place. In particular, the method makes it possible, in an arrangement comparable to that presented for introducing exogenous sequences into the E1 region, to introduce exogenous sequences into the E4 region using appropriate plasmids. In this case, the recombination at place between a parental plasmid (which possesses the left-hand ITR and encapsidation regions which is preceded by a restriction site for the enzyme PacI and by a truncated adenoviral genome in the vicinity of the E4 region) and a shuttle plasmid (which possesses a sequence close to the E4 region which is identical to the parental vector—and which will be involved in the recombination event—followed by the cassette for expressing the sequence of interest, then by the right-hand ITR region and by a unique PacI site).

According to one particularly advantageous embodiment, the genome of the adenovirus which is produced also lacks all or part of the E3 and/or E4 and/or IVA2 region. These additional deletions increase the safety of the vector and enlarge its capacity. Preferably, the adenoviral genome lacks a part of the E4 region comprising at least the ORF3 and ORF6 open reading frames. The adenoviral genome can also be modified as described in Application FR 9413355, which is hereby incorporated by reference, so as to avoid the risks of contamination with replicating particles. In one particular embodiment, the resulting complete recombinant adenoviral genome is a so-called gutless genome, that is a genome which lacks any coding region of the adenovirus. In this embodiment, the truncated genome of the plasmids comprises, on the one hand, an ITR and the encapsidation region and, on the other hand, an ITR, with it being possible for the region of homology to consist of the heterologous nucleic acid itself or of an artificial sequence which is included in each plasmid.

In this regard, the region of homology which is present in each plasmid can, in a general manner, be a nonviral sequence, which is or is not artificial, which enables homologous recombination to take place.

The recombinant genome can also include cassettes which are excised in vivo (WO97/47757) or modified gene sequences (genes for fibre or penton) which enable the tropism of the virus to be altered. Furthermore, the genomic organization of the virus can also be modified in order to improve the safety of the viruses which are produced (WO96/13596).

As pointed out above, the recombinant adenovirus genome is advantageously flanked by one or more restriction sites which are not present in the said genome. This or these sites enable the recombinant adenoviral genome to be excised from the plasmid simply and efficiently. Since the genome sequence of the adenovirus is known and accessible, the skilled person can use routine experiments to select restriction sites which are not present in this genome. The PacI, NspV and SwaI (in the case of Ad5) or SnabI (in Ad2) sites may be mentioned by way of example. It is also possible to make certain sites unique by modifying the sequence of the adenoviral genome. Thus, other enzymes can be used if the corresponding restriction sites are suppressed, modified or deleted in the adenoviral sequence which is constructed in *E. coli*. The sites can be positioned directly adjacent to the ends of the adenoviral genome or spaced by a few base pairs from the ends.

The plasmids according to the invention can be constructed using adenoviruses of diverse origins. Thus, various adenovirus serotypes, whose structure and properties vary somewhat, have been characterized. Of these serotypes, preference is given to using human type 2 or type 5 adenoviruses (Ad 2 or Ad 5) or adenoviruses of animal origin (see Application WO 94/26914) within the context of the present invention. Adenoviruses of animal origin which can be used within the context of the present invention and which may be mentioned are adenoviruses of canine, bovine, murine (example: Mav1, Beard et al., Virology 75 (1990) 81), ovine, porcine, avian or simian (example: SAV) origin. The adenovirus of animal origin is preferably a canine adenovirus, more preferably a CAV2 adenovirus [Manhattan strain or A26/61 (ATCC VR-800), for example]. According to a particular embodiment of the invention, the adenovirus employed is an adenovirus of human origin. According to another advantageous embodiment, the adenovirus is an adenovirus of animal origin.

Homologous Recombination and Production of Viruses

The techniques known to the skilled person can be used to carry out the step of homologous recombination (which enables the complete genome to be reconstructed) by transfecting (or cotransfecting) the plasmids into an appropriate cell, preferably a prokaryotic cell. In one particular embodiment, the homologous recombination is carried out in *E. coli* using a polA strain in order to select the homologous recombination events. It is obvious that these constructs can also be prepared in the absence of systems for selecting recombination events. This is because these recombination events can be screened for by making minipreparations, or by the loss or acquisition of a marker, or be screened for using radioactive probes which are specific for the junctions which are obtained or lost. Moreover, other techniques also exist for selecting homologous recombination events in *E. coli*. Those which may be mentioned are the use of plasmids whose replication is temperature-sensitive (Hamilton et al., 1989), the use of non-replicating circular molecules (described, for example, by Slater and Maurer, 1993), the use of strains in which the vector employed does not replicate (Miller and Mekalanos, 1988, Zeef et al., 1994), etc. Any of these systems can be used instead of polA strains and transformation with a plasmid derived from pBR322, or its many derivatives, or other plasmids whose replication is PolA-dependent, or else plasmids which do not replicate in *Escherichia coli*.

Another part of the subject-matter of the present application relates to any prokaryotic cell which harbors a plasmid as defined above. The cell can, in particular, be any bacterium for which a vector system exists in which recombinant DNA can be introduced. Examples which may be mentioned are *Escherichia coli, Salmonella typhimurium, Bacillus subtilis, Pseudomonas putida, Pseudomonas aeruginosa, Agrobacterium tumefaciens, Rhizobium meliloti* or the bacteria of the genus *Streptomyces*. These cells are advantageously obtained by transformation using the techniques known to the skilled person. The transformation can, in particular, be effected by means of the transformation technique using $CaCl_2$ (Dagert and Ehrlich, 1979), or by that developed by Hanahan et al. (1983) or by any technique which is derived therefrom (Maniatis et al., 1989), as well as by electrotrans-formation (Wirth et al., 1989). See also general molecular biological techniques below.

Another part of the subject-matter of the present invention resides in a process for producing recombinant adenovirus genomes. In accordance with this process, prokaryotic cells such as described above are cultured and the plasmids are then recovered in a second step. The culture is advantageously carried out for a time which is sufficiently long for producing appropriate quantities of plasmid. The plasmid can be recovered using any technique known to the skilled person for preparing plasmid DNA. Thus, it can be recovered by preparing a clear lysate followed by centrifugation in a cesium chloride gradient (Maniatis et al., 1989). It is possible to use other techniques which resort to other methods of lysis using triton X-100, for example (Ausubel et al., 1987), or else an anion exchange column after the step of lysis and separation of the plasmid DNA from the majority of the chromosomal DNA and the proteins. The plasmids which have thus been recovered can then be purified and treated in the presence of the restriction enzyme which corresponds to the sites bordering the viral genome. This enables a linear recombinant adenovirus genome, which can be used directly for the clonal production of recombinant viruses, to be generated in one single step.

In this regard, a first method for preparing the recombinant viruses consists in transfecting the viral genome which has been produced from the plasmids of the invention into a competent encapsidating cell line, that is a cell line which carries in trans all the functions which are required for complementing the defective virus. These functions are preferably integrated into the genome of the cell, thereby reducing the risks of recombination and conferring increased stability on the cell line.

A second approach consists in cotransfecting, into an appropriate cell line, the recombinant genome which has been prepared and the DNA of one or more helper viruses or plasmids. When this method is used, it is not necessary to have available a competent cell line which is able to complement all the defective functions of the recombinant adenovirus. This is because some of these functions are complemented by the helper virus(es). This or these helper viruses are themselves defective.

A cell line which can be used and which may in particular be mentioned is the human embryonic kidney cell line 293 (Graham et al., J. Gen. Virol, 36 (1977) 59). This cell line contains, in particular, integrated into its genome, the left-hand part of the genome of the human Ad5 adenovirus (12%). The transfection can advantageously be effected directly using the plasmid digestion product obtained in accordance with the above-described process, without any step of purifying the adenoviral genome. Examples of other cell lines are cell lines which are produced from embryonic retina cells (HER), from liver cells, etc. The cell lines can be cell lines which complement the E1 (293, PERC-6 cells), E1 and E4 (IGRP2), and E1 and E2 functions, etc. These cell lines have been described in the prior art and can be used by the skilled person.

The adenoviruses which are produced in this way can be isolated or purified using the techniques known to the skilled person (cesium chloride, chromatography, etc.). They can be used in a variety of applications, such as the production of therapeutic or prophylactic products in vitro, ex vivo or in vivo, or else for functionally analyzing the genome (and the composition of libraries).

The advantages of using the novel process are as follows: generation of the recombinant more readily and with greater speed and the absence of any requirement for a screening step linked to the numerous selection systems which are imposed on the process and on the structure of a nonfunctional parental vector.

Contrary to the known, described processes, the robustness of the process is based on the simultaneousness of the selection pressures, which leads, in a single step, to the selection of the only final plasmid which carries the functional adenoviral genome. The generation of a new recombinant vector in a single step substantially reduces the necessary working time as compared with the known processes. Since there is no need for any screening step, the quantity of work required is considerably reduced as compared with the known processes. Furthermore, the absence of any need for screening opens the way for simultaneously generating large numbers of recombinant adenoviral vectors through one single intermediate.

Another advantage of the process of the invention resides in the nonviable aspect of the two plasmids which are recruited for generating the final plasmid carrying the functional genome. Neither of the two initial plasmids separately possesses all the functions which would enable it to generate a functional adenoviral genome. In addition, in the extreme case of an escape in the selections imposed (antibiotics), and if two types of construct (the desired construct and the initial plasmids) were to coexist after the recombination in the bacterial strain, this result would not have any effect on the generation of the desired recombinant vector once this mixture had been transfected into the eukaryotic producer cell. This is because only the desired construct, resulting from the homologous recombination, is viable, and propagates in the eukaryotic producer cell, with the initial plasmids being nonviable (absence of at least one ITR region in each plasmid).

The abovementioned features of the invention process contribute toward simplifying the construction of adenoviral vectors and open the possibility of generating recombinant vectors at the high output rate. This can relate to simultaneously constructing recombinant adenoviral vectors which carry known sequences whose function it is wished to validate or to simultaneously constructing a set of recombinant vectors which carry sequences of unknown nature whose function it is wished to discover. In this latter case, the sets of vectors are referred to as adenoviral expression libraries.

In a Gene Therapy Application

The adenoviruses can be used in therapeutic applications. For this purpose, the heterologous nucleic acid can comprise one or more therapeutic genes and/or one or more genes encoding antigenic peptides.

The therapeutic genes which can be transferred in this way are all genes whose transcription and, where appropriate, translation in the target cell generate products which have a therapeutic effect.

The product can be a product which is homologous with regard to the target cell (that is a product which is normally expressed in the target cell when this latter does not exhibit any pathology). In this case, the expression makes it possible, for example, to compensate for an insufficient expression in the cell or for the expression of a protein which is inactive or weakly active due to having been modified, or else to overexpress said protein. The therapeutic gene can also encode a mutant of a cell protein which has an increased stability, a modified activity, etc. The product can also be heterologous with regard to the target cell. In this case, an expressed protein can, for example, complement or supply an activity which is deficient in the cell, thereby enabling the latter to combat a pathology.

Therapeutic products which may more specifically be mentioned are enzymes, blood derivatives, hormones, lymphokines: interleukins, interferons, TNF, etc. (WO93/19191), growth factors, neurotransmitters or their precursors or enzymes for synthesizing them, trophic factors: BDNF, CNTF, NGF, IGF, GMF, aFGF, bFGF, NT3, NT5, etc.; apolipoproteins: ApoAI, ApoAIV, ApoE, etc. (WO94/25073), dystrophin or a minidystrophin (FR 9111947), tumor-suppressing genes: p53, Rb, Rap1A, DCC, k-rev, etc. (WO9424297), genes encoding factors involved in coagulation: factors VII, VIII and IX, suicide genes (TK, etc.), etc.

The therapeutic gene can also be a gene or an antisense sequence whose expression in the target cell makes it possible to control the expression of cellular genes or the transcription of cellular mRNAs. Sequences of this nature can, for example, be transcribed, in the target cell, into RNAs which are complementary to cellular mRNAs and thereby block translation of the latter into protein, in accordance with the technique described in Patent EP 140 308.

As pointed out above, the nucleic acid of interest can also comprise one or more genes encoding an antigenic peptide which is able to generate an immune response in man. In this particular embodiment, the invention therefore makes it possible to prepare vaccines for immunizing humans, in particular against microorganisms or viruses. The vaccines can, in particular, be antigenic peptides which are specific for the Epstein barr virus, for the HIV virus, for the hepatitis B virus (EP 185 573), for the pseudorabies virus, or else specific for tumors (EP 259 212).

Usually, the nucleic acid of interest also comprises sequences which enable the therapeutic gene and/or the gene encoding the antigenic peptide to be expressed in the infected cell. These sequences can be sequences which are naturally responsible for expressing the gene under consideration when these sequences are able to function in the infected cell. These sequences can also be sequences of different origin (sequences which are responsible for expressing other proteins, or even synthetic sequences). In particular, the sequences can be promoter sequences for eukaryotic or viral genes. For example, the sequences can be promoter sequences which are derived from the genome of the cell which it is desired to infect. Similarly, the sequences can be promoter sequences which are derived from the genome of a virus, including the adenovirus employed. The promoters of the E1A, MLP (Major Late Promoter), CMV (Cytomegalovirus), RSV (Rous Sarcoma Virus), etc. genes may, for example, be mentioned in this regard. In addition, these sequences for expression can be modified by adding sequences for activation, for regulation, etc. Preferably it will be possible to use promoters of the Tet on/off or off/on type, which can be regulated by tetracycline, or promoters which can be induced by ecdysone or dexamethasone. Furthermore, when the inserted gene does not comprise any sequences for expression, it can be inserted into the genome of the defective virus downstream of such a sequence. Finally, the nucleic acid of interest can also comprise, in particular upstream of the therapeutic gene, a signal sequence which directs the synthesized therapeutic product into the secretion pathways of the target cell. While this signal sequence can be the natural signal sequence of the therapeutic product, it can also be any other functional signal sequence or an artificial signal sequence.

The present invention also relates to any pharmaceutical composition which comprises one or more recombinant adenoviruses which has been prepared in accordance with this process. The pharmaceutical compositions of the invention can be formulated with a view to being administered topically, orally, parenterally, intranasally, intravenously, intra-muscularly, subcutaneously, intraocularly, transdermally, etc.

Preferably, the pharmaceutical composition contains excipients which are pharmaceutically acceptable for an injectable formulation. These excipients can, in particular, be sterile, isotonic saline (monosodium or disodium phosphate, sodium, potassium, calcium or magnesium chloride, etc., or mixtures of such salts) solutions or dry, in particular lyophilized, compositions which, by the addition of sterilized water or physiological saline as the case may be, enable injectable solutions to be constituted.

The doses of virus employed for the injection can be adjusted in accordance with a variety of parameters, in particular in accordance with the mode of administration employed, the pathology concerned, the gene to be expressed or the sought-after duration of the treatment. Generally speaking, the recombinant adenoviruses in accordance with the invention are formulated and administered in the form of doses of between $10^4$ and $10^{14}$ pfu, preferably from $10^6$ to $10^{10}$ pfu. The term pfu (plaque forming unit) corresponds to the infectious power of a virus solution and is determined by infecting an appropriate cell culture and measuring, usually after 15 days, the number of plaques of infected cells. The technique for determining the pfu titer of a viral solution are well documented in the literature.

Depending on the heterologous DNA sequence which is inserted, the adenoviruses of the invention can be used for treating or preventing a large number of pathologies including genetic diseases (dystrophy, cystic fibrosis, etc.), neurodegenerative diseases (Alzheimer's, Parkinson's, ALS, etc.), cancers, pathologies linked to coagulation disorders or dyslipoproteinemias, pathologies linked to viral infections (hepatites, AIDS, etc.), etc.

In an Application for Producing Recombinant Proteins

The invention process makes it possible to generate adenoviral vectors which enable recombinant proteins to be produced, in particular in human cells in culture. The recombinant proteins can be proteins such as human serum albumin, human interferons, human antibodies, human insulin, hematopoietic factors, factors such as factor IX or factor VII, thrombolytic factors such as tissue plasminogen activator, various growth factors, trophic factors, cytokines, peptides of the central nervous system, opioids, enzymes and viral antigens, and also proteins from other organisms such as that of plants.

In a Functional Genomic Application:

Using the same preparation tools as mentioned above, the process is exploited in an application for validating or discovering novel targets in the sense understood by the pharmaceutical industry.

The present invention also relates to any exploitation of a composition using the described method. In particular, beyond that, any preparation which makes it possible to obtain and integrate a nucleic acid, whatever their nature, into a first shuttle plasmid within the meaning of the invention and to use said plasmids for generating one or many recombinant adenoviruses using the various methods of automation. These recombinant adenoviruses can then be used in numerous in vitro and in vivo models for evaluating the functional ability of the sequences which they carry. The functional ability of the sequences carried by the recombinant adenoviruses which have been generated maybe evaluated using one of the large number of functional tests which are available to the skilled person.

Part of the subject-matter of the invention therefore also resides in a process for preparing adenoviral expression libraries, which process comprises the following steps:
  constructing a primary library in a shuttle vector as described above,
  transforming a bacterial culture with said primary library, in the presence of a parent plasmid according to the invention,
  introducing the resulting plasmids, or the complete adenoviral genomes following excision by enzymic digestion, into an adenovirus-producing cell.
  where appropriate, infecting a biological material comprising cells in order to analyze the clones in the library.

This process therefore comprises a first step of preparing a primary library of nucleic acids in the shuttle plasmid of the invention before applying the invention and using the adenoviral library in an experimental model. A primary library of this nature can be constituted in the plasmid of the invention (shuttle plasmid) using molecular biological methods known to the skilled person. In particular, the primary library can be constructed by carrying out the following operations in succession: a) obtaining mRNA (or total RNA) from a cell population, b) preparing the DNA which is complementary to the mRNA population which has been isolated, c) where appropriate, preparing a nucleic acid library in which the cDNA molecules are placed under the control of a strong promoter or, more especially, under the control of a regulatable promoter, and d) incorporating the cDNA molecules (or the expression cassette) into the shuttle plasmid of the invention.

The present invention therefore also relates to a nucleic acid library which is cloned into a vector or shuttle plasmid as previously described.

In the second step, cotransformation of the primary library of shuttle plasmids together with a parental plasmid as described in the invention results in a library of plasmids which carry functional adenoviral genomes. This step can be effected either by simultaneously cotransforming the plasmids into the bacteria or by carrying out sequential transfections. Thus, the parent plasmid can be introduced into the bacteria first of all, with the shuttle plasmids then being transfected subsequently.

In the third step, the plasmids (or the excised functional recombinant genomes are transfected into a transcomplementing cell, thereby enabling a library of recombinant adenoviruses to be generated. Preference is given to isolating and/or purifying the resulting plasmids and to the recombinant genomes being excised by treatment with the appropriate enzyme (or enzymes) which do(es) not cut the adenoviral genome.

In the fourth step, infection of a chosen cell population (or of a biological material) with the aid of the library of recombinant adenoviruses enables the biological or functional properties of the clones in the library to be analyzed. For this, the chosen, and infected, cell population can be placed under conditions which enable the nucleic acid to be expressed and a sought-after phenotype thus to be identified by studying the cell population. It is then possible to go back to the vector which induces the phenotype and thus to characterize the DNA which conferred the sought-after phenotype.

In order to make the studies of functional ability more robust, the clones are advantageously treated separately and not in a pool. Thus, the primary library clones in the shuttle plasmid are transformed individually, in microplates, into the bacterium, which already possesses the parental truncated adenoviral plasmid. The DNA molecules which are produced by growing in microplates under selection pressure (antibiotics) are purified and transfected into the eukaryotic producer cell after the genomes have been excised using the chosen enzyme (for example PacI). A process of this nature is depicted diagrammatically in FIG. 2.

According to a preferred embodiment of the process for preparing adenoviral expression libraries of the present invention, it is possible to use the Gateway® cloning technology, which was developed by Life Technologies, Inc. (LTI, Rockville, Mass., USA) and which makes it possible, in particular, to simultaneously generate a set of adenoviruses which are carrying inserts which are derived, for example, from a complementary DNA library or from a group of sequences which have been characterized and selected using various methodologies which are well known to the skilled person.

The Gateway® cloning technology, which is described, inter alia, in the U.S. Pat. No. 5,888,732, makes it possible to transfer inserts between, for example, two plasmid vectors during an in vitro reaction owing to recombination reactions at the specific sites attL, attR, attB and attP of the lambda (λ) bacteriophage of *Escherichia coli*. The insertion of a gene no longer requires the presence of appropriate restriction sites within the vector but only the presence of short recombination sequences termed att sequences.

The Gateway® cloning system consists, on the one hand, in performing what is termed an LR reaction, during which an Entry clone, containing an insert of interest surrounded by the attL sites, recombines with a Destination clone, containing the attR sites, in order to generate an Expression clone. The insert of interest, which is carried by the Entry clone, is then transferred into an Expression vector, which is derived from the Destination clone and which contains the attB sites. On the other hand, the Gateway® system consists in performing the reverse reaction, which is designated the BP reaction and during which the Expression clone, containing an insert of interest surrounded by the attB recombination sites, recombines with a Donor vector, containing the attP sites, in order to give the Entry clone, which contains the attL sites.

More specifically, according to a first strategy, it is possible to modify a shuttle plasmid for example pJJ1, as previously described, in order to generate a plasmid which is compatible with the Gateway® system and which possesses the appropriate att sites. According to this first approach, the att sites are preferably introduced between the promoter (CMV) and the SV40 polyadenylation site of the expression cassette of the shuttle plasmid. The resulting plasmid is termed a Destination plasmid, in accordance with the terminology of the Gateway® technology, and can then enter into a reaction with the Entry clones of the Gateway® technology. Consequently, any insert which is derived from a DNA library or a group of selected sequences, and which is cloned into an Entry clone or vector, can be transferred into the shuttle plasmid, within the meaning of the invention, in order to give an Expression shuttle plasmid which can be used in the invention for generating the corresponding adenoviral vector.

According to a second strategy, the complete adenoviral plasmid is modified in order to be compatible with the Gateway® technology. It is therefore a matter of introducing the appropriate att sites into the adenoviral genome-carrying plasmid in order to make it possible to carry out the reactions described in the Gateway® cloning system. Preferably, the att sites are introduced, in place of the E1 region of the adenoviral genome, between a promoter and a polyadenylation sequence. This strategy thus makes it possible to generate adenoviral genome-carrying plasmids which contain varied inserts which were originally present in the Entry clones. These inserts may be derived from creating complementary DNA libraries, inserts which represent the genes of one and the same family, or inserts of any other origin. An adenoviral genome-carrying plasmid is generated, which plasmid is modified and possesses the att sequences and is a Destination clone within the meaning of the Gateway® technology; this plasmid is designated pAdDEST (Example 6, FIG. 10). The Destination clone which is thus obtained, i.e. pAdDEST, can react with any Entry clone in order to generate an Expression plasmid carrying the adenoviral genome: pAdExp as described below in Example 6 and in FIG. 11.

The invention thus represents a novel method for validating or identifying a sequence which is associated with a physiological or genetic effect inducing a characteristic phenotype. The sequence can, more specifically, be a gene which gives rise to a genetic defect or a gene which could be indicative or characteristic of a genetic anomaly.

While, in an application for validating or determining the function of one or more sequences within the context of a functional genomic activity, the sequences can be of any natures, in particular those sequences mentioned above, they can also be derived from populations of any sequences of nature which are unknown and multivarious. These sequences can be juxtaposed in different cassettes in order to be introduced subsequently into the desired adenoviral genome.

These sequences can be derived from any type of living cell or be produced artificially by various methods such as de nova synthesis, mutagenesis, combining sequences, etc.

Within the context of the present invention, a large number of libraries can be used as the source of nucleotide sequences, including, but not limited to, genomic DNA libraries (in particular libraries of chromosomal regions—including, for example, libraries in YACs or BACs), cDNA libraries and synthetic DNA libraries, whether these libraries are standardized or not and prepared from different living tissues for sense or antisense expression, from sequences which are generated randomly and which are able to generate a variety of peptides, from degenerate sequences prepared from a known sequence, from a mosaic sequence of known sequences, etc.

In particular, the primary sequences to be studied can generate antisense molecules or elements for gene suppression. These are sequences which, on being expressed, can inactivate a particular gene in the biological system under study. The sequence can be a ribozyme sequence.

The sequences employed for creating the library can be derived from a variety of synthetic processes. In particular, the simulation of a controlled molecular evolution which uses recombination makes it possible to generate a variety of genes using identified mechanisms of evolution (Curr. Op. in Biotech. 1997, 8: 724-733).

The sequences employed for creating the libraries can also be derived from the bioinformatic analysis of databases which record the data from the human genome. These sequences can be selected using analysis of gene expression which are obtained by various methods (EST, Microarrays, DNA chips, differential display) TIBtech 1996, 14 p 294-298; Nature Biotechnology 1998, 16, p 27-31.

In particular, the process makes it possible to generate an adenoviral library for expressing randomized peptide sequences. This then facilitates the selection and identification of random peptide sequence which are able to bind to a protein of interest. A library of oligonucleotides of random sequence is introduced into a (polylinker) site corresponding to a flexible loop of a natural or synthetic protein so that the peptides are presented on the surface of the protein. It can be a matter of presenting these peptides intracellularly (Colas et al., 1996, Nature 380: 548-550) or at the surface of the cell (Tramonto et al., 1994, J. Mol. Recognit. 7:9-24). Finally, the peptides can be presented on the outside of the cell by inserting a secretion signal into the expression cassette (Rice et al., 1992, PNAS 89, 5467-5471).

One or more sequences of interest can be integrated into the vector.

It can in the end be a matter of evaluating a combination of sequences (expression cassette) or of coexpressing the sequence of interest with another gene of interest, for example a marker gene. It can then be decided either to use polycistronic sequences or to place the sequence(s) to be expressed in a location in the adenoviral genome which are different from that of the sequence of interest. A variety of polycistronic sequences can be used. The IRES elements enable two or more open reading frames to be translated efficiently from one single mRNA. More especially, one open reading frame encodes the protein of interest (being derived from a cDNA library) while the other open reading frame encodes a marker such as GFP.

The process makes it possible to use excision/integration systems which are linked to an enzyme activity. This system can be the CRE-Lox system (Baubonis et al., Nucl. Acids Res. 21:2025-2029), the FLP recombinase-FRT system (Dang et al., Dev. Gent. 13; 367-375), the *Moraxella lacunata* Piv system (Lenic et al., 1994, J. Bacteriol. 176-4160) or the lambda integrase system (Kwon et al., 1997 Science 276, 126). More specifically, a sequence or the cassette expressing the cDNA is attached to a replicating episomal vector is excised by the Cre-lox system of the adenoviral genome and will be transmitted to the dividing infected cells (WO97/47757).

The process facilitates the detection of DNA-protein interactions. The library then corresponds to a population of sequences which are able to bind to DNA. These sequences are either polypeptides which are derived from proteins which are naturally able to bind to DNA or artificial polypeptides. The sequence is sought which is most specific for a given DNA sequence.

The process enables protein-protein interactions to be detected. Use is made of the ability of the adenoviral vector to coinfect. The LacZ complementation test is preferably employed (PNAS 1997, 94, 8405-8410). The cell system is coinfected with the first construct and the cDNA library.

A large and varied number of functionality tests can be implemented for analyzing the adenoviral expression library of the invention.

Use can be made, for example, of complementation tests, which consist in identifying the nucleotide sequence derived from the library whose expression leads to a sought-after cell phenotype. More specifically, the adenoviral expression library can be used to infect a human cell which is deficient in a phenotypic trait. Analysis of the infected cells and pinpointing of the cells which then display the sought-after phenotypic trait. Analysis of the cDNA carried by the virus responsible for the appearance of the phenotypic trait. It is also possible to measure the disappearance of a phenotypic trait after infection, resulting from an antisense activity or a functional knock-out.

The process facilitates the study of the mode of action of a chemical molecule in a biological system. The adenoviral expression library is used to infect the cells of the biological system which responds to the action of the drug. After the infection, the effect of the drug may be unchanged, increased or inhibited. In the latter two cases, analysis of the cDNA molecules carried by the viral genomes facilitates the discovery of the intracellular and/or extracellular pathways involved in the effect of the chemical compound.

The process of the invention can thus be implemented for
  searching for nucleic acids (targets) which make it possible to circumvent the effects of p53 in the process of stopping growth and apoptosis.
  identifying cytokines
  identifying synthetic peptides which affect cellular processes
  searching for molecules which are able to present peptides extracellularly
  identifying targets for tumor cells which do not exhibit any specific tumor suppressants.
  identifying genes involved in the process of metastases.
The invention also relates to a kit which comprises:
  a shuttle plasmid comprising a first truncated adenovirus genome, and
  a parent plasmid comprising a second truncated adenovirus genome,
with the two plasmids being able to produce, by means of homologous recombination between the two truncated adenovirus genomes, a final plasmid which comprises a complete linear recombinant adenovirus genome which is flanked by one or more restriction sites which is/are not present in said genome.

The present invention will be more completely described with the aid of the examples which follow and which should be regarded as being illustrative and not limiting.
General Cloning, Molecular Biological and Cell Biological Techniques.

The conventional molecular biological methods such as the centrifugation of plasmid DNA in a cesium chloride-ethidium bromide gradient, digestion with restriction enzymes, gel electrophoresis, transformation into *E. coli*, precipitation of nucleic acids, etc., are described in the literature (Maniatis et al., 1989).

The enzymes were supplied by New England Biolabs (Beverly, Mass.). For the ligations, the DNA fragments are separated according to their size on 0.8 to 1.5% agarose gels, purified using GeneClean (BIO101, LaJolla Calif.) and incubated overnight at 14° C. in a 50 mM Tris-HCl, pH 7.4, 10 mM MgCl$_2$, 10 mM DTT, 2 mM ATP buffer in the presence of phage T4 DNA ligase.

The ligated DNAs are used for transforming the *E. coli* strain TG1 [Δ(lac proA,B), supE, thi, hsdD5/F' traD36, proA$^+$, B$^+$, lacI$^q$, lacZΔM15] (Maniatis et al., 1982), which has been rendered competent, *E. coli* Top10 strain cells (TOP10 One Shot kit, Invitrogen, Netherlands) or else the *E. coli* polA strain SF800 (Heffron et al., 1977).

PCR (Polymerase Chain Reaction) amplification was also carried out as described in Maniatis et al., 1989, using the following specifications:

denaturation temperature 95° C., hybridization temperature 55° C., extension temperature 72° C. This cycle was repeated 25 times in a PTC-200 Peltier Thermal Cycler (MJ Research, Mass., US).

The oligonucleotides were synthesized by the company GENSET (Evry, France). The sequencing was carried out by the company ESGS (Evry, France).

EXAMPLES

Example 1

Constructing Parental Plasmids

This example describes obtaining a human type 5 adenoviral genome, which is truncated in its 5' part and deleted for the E1 and E3 regions, and whose 3' part is flanked by a unique restriction site, in a plasmid which belongs to incompatibility group P and which replicates in *E. coli*.

The plasmids according to the present invention can be constructed in different ways. According to a preferred method, the plasmid pOSE17-00 is constructed in accordance with the EDRAG methodology (FR2,730,504) using the plasmids pXL3215 and pJJ301. Plasmid pXL3215 contains all of the AD genome (less two deletions in the E1 and E3 regions) and possesses a cassette for expressing the LacZ gene, under the control of the RSV promoter, in the E1 region. Plasmid pXL 3215 is a derivative of plasmid pXL2689 and contains the origin of replication from plasmid RK2 and the gene for resistance to tetracycline (J. Crouzet PNAS, 1997).

Figure 3:
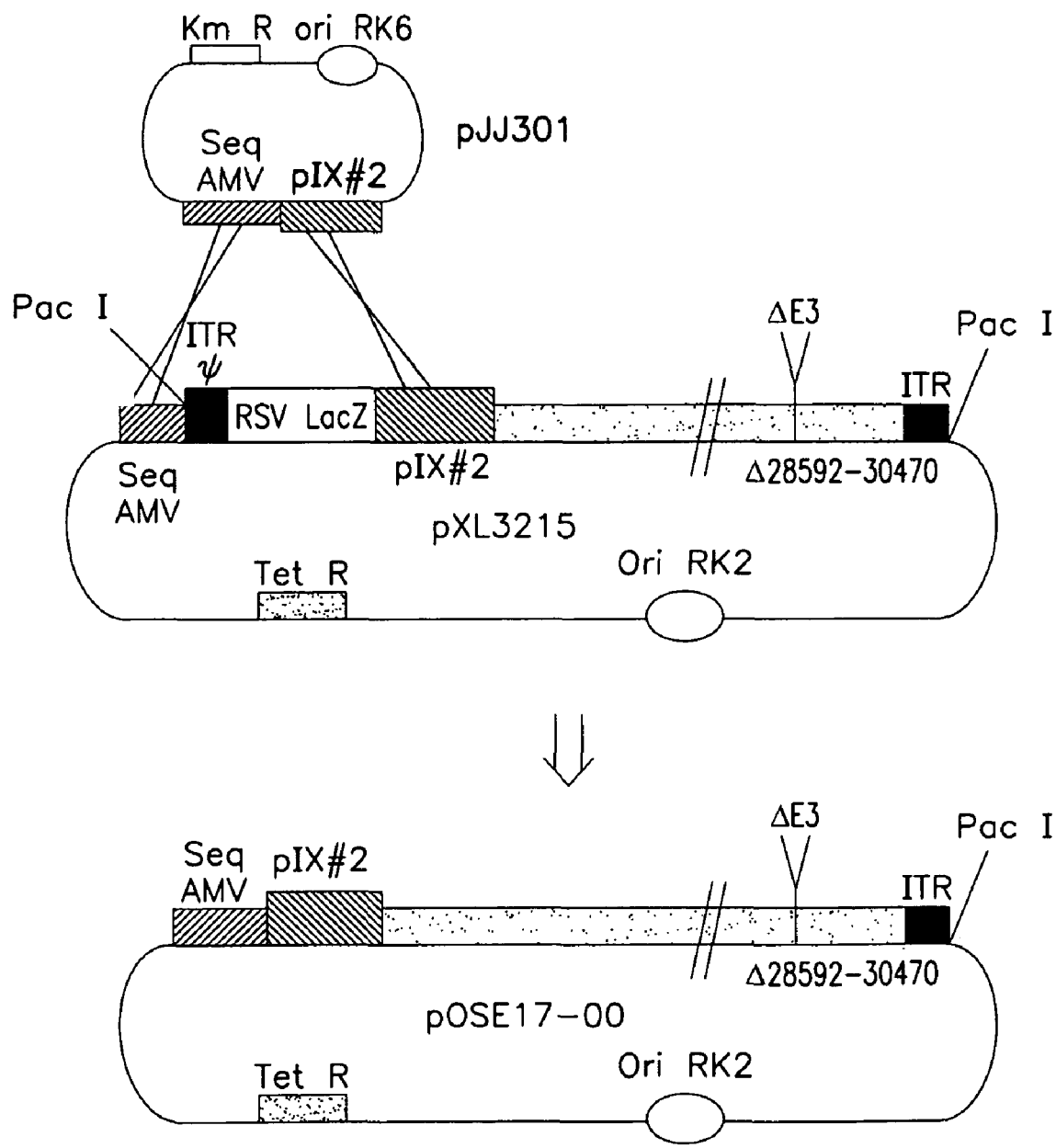
FIG. 3 Using the EDRAG technology (Crouzet et al.) to obtain the parental plasmid according to the invention, which plasmid carries an incomplete, and therefore nonfunctional, adenoviral genome sequence. Maps of plasmids pJJ301, pXL3215 and plasmid pOSE17-00.

Plasmid pJJ301 possesses an RK6 origin of replication and is unable to replicate in *E. coli* pir-strains. Plasmid pJJ301 possesses the gene for resistance to kanamycin. Plasmid pJJ301 possesses a region which is homologous with the beginning of the adenoviral genome carried by pOSE17-00. This region is a special version of the pIX region which is termed syngen#2 and which is described in (WO99/25861). Upstream of this sequence, a sequence is inserted which is homologous with the region upstream of the complete adenoviral genome in plasmid pXL3215. Double recombination between plasmids pXL3215 and pJJ301 gives rise to pOSE17-00. This plasmid pOSE17-00 corresponds to a parental plasmid within the meaning of the invention process and is shown diagrammatically in FIG. 3.

Other parental plasmids (pOSE10-00, pOSE30-00, pOSE37-00) have been constructed using the same scheme, thereby generating adenoviral genomes which are deleted in the E1 and E3 regions (in a wild-type pIX region version or in a degenerate pIX version (WO99/25861) or adenoviral genomes which are deleted in the E1, E3 and E4 regions (in a wild-type pIX region version or in a degenerate pIX version (FIG. 4)).

Example 2

Constructing Shuttle Plasmids

This example describes obtaining a shuttle plasmid which carries the 5' region of the human type 5 adenoviral genome (ITR region and encapsidation region), preceded by a Pac I restriction site.

Figure 5:
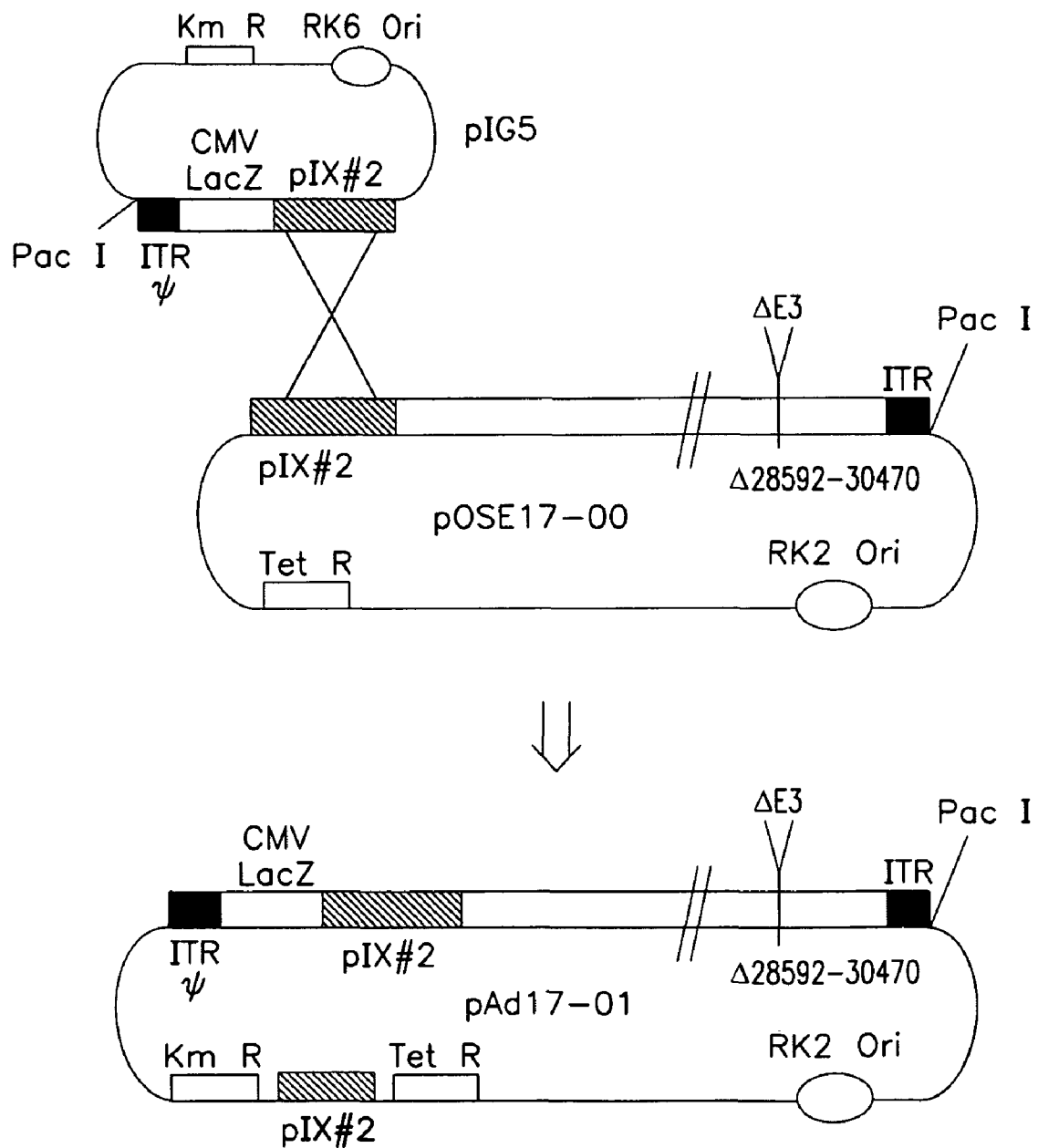
FIG. 5 Using the invention process to obtain a recombinant adenoviral genome which carries a cassette for expressing the LacZ gene. Maps of the shuttle plasmid pIG5, the parental plasmid pOSE17-00 and the final plasmid pAd17-01. Maps of plasmids pIG5, pOSE17-00 and pAd17-01.

Said plasmid possesses an RK6 origin of replication and is unable to replicate in *E. coli* which cannot transcomplement for the pir protein. Said plasmid pIG5 contains a cassette for expressing LacZ preceding a sequence which is homologous with a sequence which is present in pOSE17-00 (sequence corresponding to a part of the pIX Iva2 region). This plasmid is termed a shuttle plasmid within the meaning of the invention; it possesses a gene for resistance to kanamycin (FIG. 5).

Example 3

Producing a Functional Recombinant Adenoviral Genome

This example describes obtaining a functional human type 5 adenoviral genome which is deleted for the E1 and E3 regions and flanked at its ends by a PacI restriction site, in a plasmid of the P incompatibility group which replicates in *E. coli* and carries a cassette for expressing the LacZ gene.

The chosen integration strategy is that of carrying out homologous recombination between pOSE17-00 and pIG5 in the *E. coli* strain. Plasmid pOSE17-00 was introduced into cells of the *E. coli* strain JM83 Rec⁺ LacZ⁻. In turn, the cells derived from a tetracycline-resistant clone were rendered competent, transformed with plasmid pIG5 and then spread on LB medium in the presence of tetracycline and kanamycin. Given that plasmid pIG5 does not replicate in the JM83 strain, the acquisition of resistances to tetracycline and kanamycin can only be brought about by a homologous recombination event taking place between the two plasmids. This can occur because the two plasmids possess the pIX region of the Ad5 genome in common. The resulting plasmid possesses the complete genome of the recombinant adenoviral vector flanked by a PacI site. Digesting with the enzymes PacI and HindIII, EcoRI or PacI and DraI makes it possible to check that the expected plasmid structure has been obtained. This final plasmid, carrying a functional adenoviral genome, was designated pAd17-01 (FIG. 5).

In the same way, plasmid pIG5 and plasmid pOSE37-00 give rise to a plasmid which carries a complete adenoviral genome which is deleted for E1, E3 and E4 and provided with a pIX region in its syngen#2 form (WO99/25861).

Figure 6:
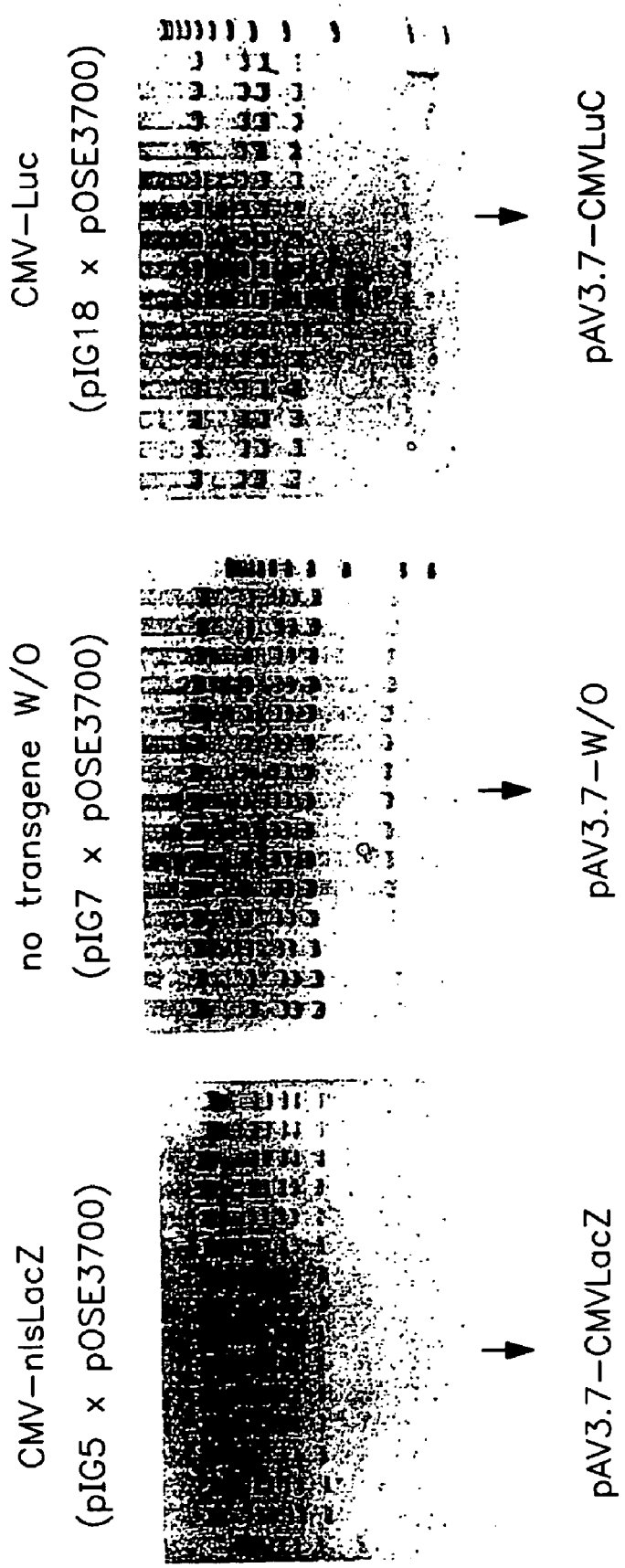
FIG. 6 Using the invention process to obtain adenoviral genomes with the aid of three different shuttle plasmids (pIG5: which carries a cassette for expressing the LacZ gene; plasmid pIG18: which carries a cassette for expressing the luciferase gene, and pIG7: without any expression cassette). Enzyme digestion of the clones resulting from the cotransformation of the shuttle plasmid and the parental plasmid.

It is also possible to use the same strategy to construct other recombinant genomes of the same family which do or do not carry an expression cassette. pIG7 and pIG18 are used and derive from pIG5: pIG7 does not have any expression cassette while pIG18 possesses a cassette for expressing the luciferase gene. Insofar as the expression cassette does not exhibit any sequence homology with the genomic sequence of the bacterial chromosome, 100% of the clones are expected to be positive. As shown in FIG. 6, 100% of the clones analyzed at the end of these experiments did indeed turn out to exhibit the expected nucleotide structures (FIG. 6).

pAd17-01 was digested with PacI, thereby liberating the genome of the recombinant adenovirus. The product of this digestion can be used as such for transfecting mammalian cells (293 cells) which are transcomplementing for the E1 functions of the adenovirus.

Example 4

Producing Recombinant Adenoviruses

Recombinant adenovirus clones can be constructed in *Escherichia coli* by (i) inserting fragments which contain one or more genes together with appropriate regulatory signals for expressing these genes in the mammalian cells under study, or (ii) by deleting certain fragments of the genome of the adenovirus or else by combining these two events, with it then being possible to obtain a stock of such a recombinant virus after producer cells have been transfected.

Plasmid pAd17-01 is purified from a culture of transformed, competent *E. coli* DH5 cells. The adenoviral genome is liberated by digesting in the presence of the enzyme PacI. The digestion product is used directly for producing the recombinant adenoviruses. For this, cells of the 293 cell line are transfected, in the presence of Effectene (Qiagen, Germany), with the product obtained from digesting pAd17-01. The recombinant adenovirus is amplified in the 293 cell line, resulting in a culture supernatant which contains unpurified recombinant adenovirus having a titer of approximately $10^{10}$ pfu/ml.

Figure 7:
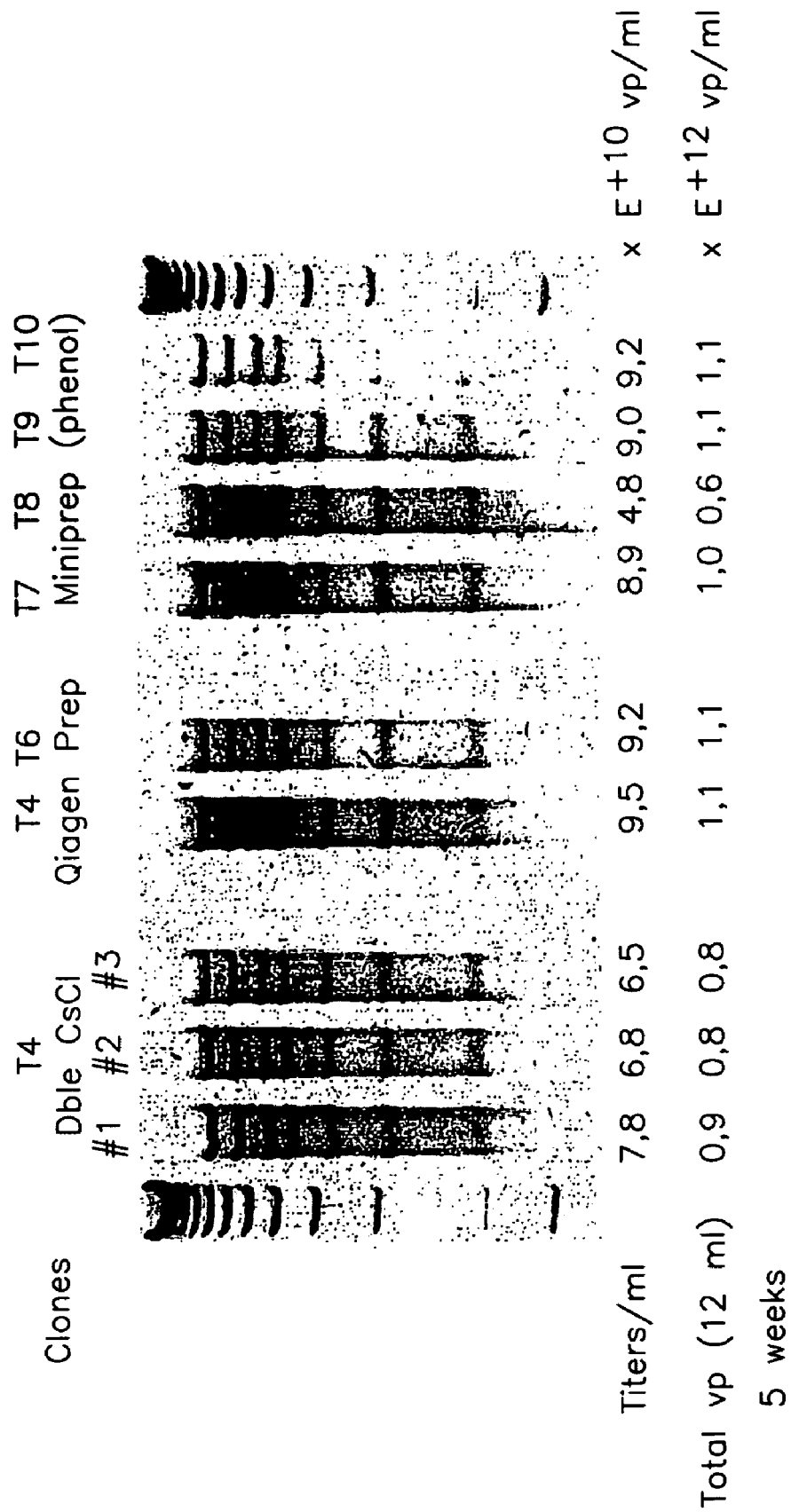
FIG. 7 Using the invention process to obtain adenoviral vectors following transfection of different clones of plasmid pAD17-01 into the 293 producer cell. Enzyme digestion of the viral DNAs which have been purified from the viruses which were amplified in the 293 cell.

The conformity of the viral DNA is verified by enzymic digestion after having purified the DNA derived from the amplified viruses (FIG. 7).

The viral particles are then purified by centrifuging on a cesium chloride gradient using known techniques (see, in particular, Graham et al., Virology 52 (1973) 456), or by means of chromatography). The adenovirus can be stored at −80° C. in 20% glycerol.

Example 5

Constructing Adenoviral Expression Libraries

The shuttle plasmid provided with the RK6 origin of replication is used for obtaining a primary library of shuttle plasmids which will then be employed, by way of homologous recombination, for obtaining a library of recombinant adenovirus genomes in the plasmid possessing the RK2 origin of replication. This plasmid library of recombinant adenovirus genomes will then be transfected into the transcomplementing producer cell in order to obtain a library of recombinant adenoviruses.

Figure 2:
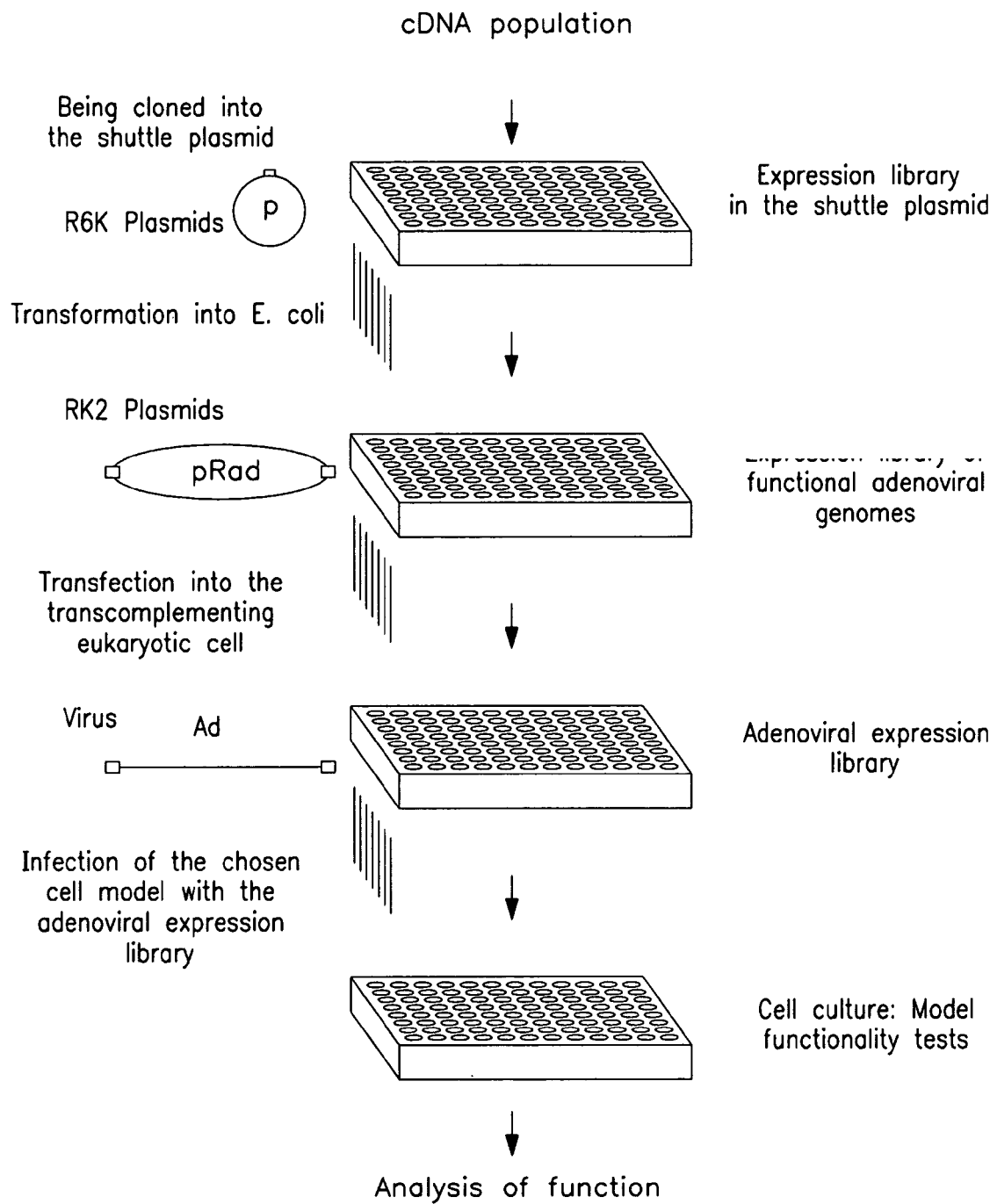
FIG. 2 Simultaneous generation of 96 recombinant adenoviruses which carry cDNAs which are derived from a cDNA library which was constructed in the shuttle plasmid. Application of the properties of OSEDRAG technology.
Figure 8:
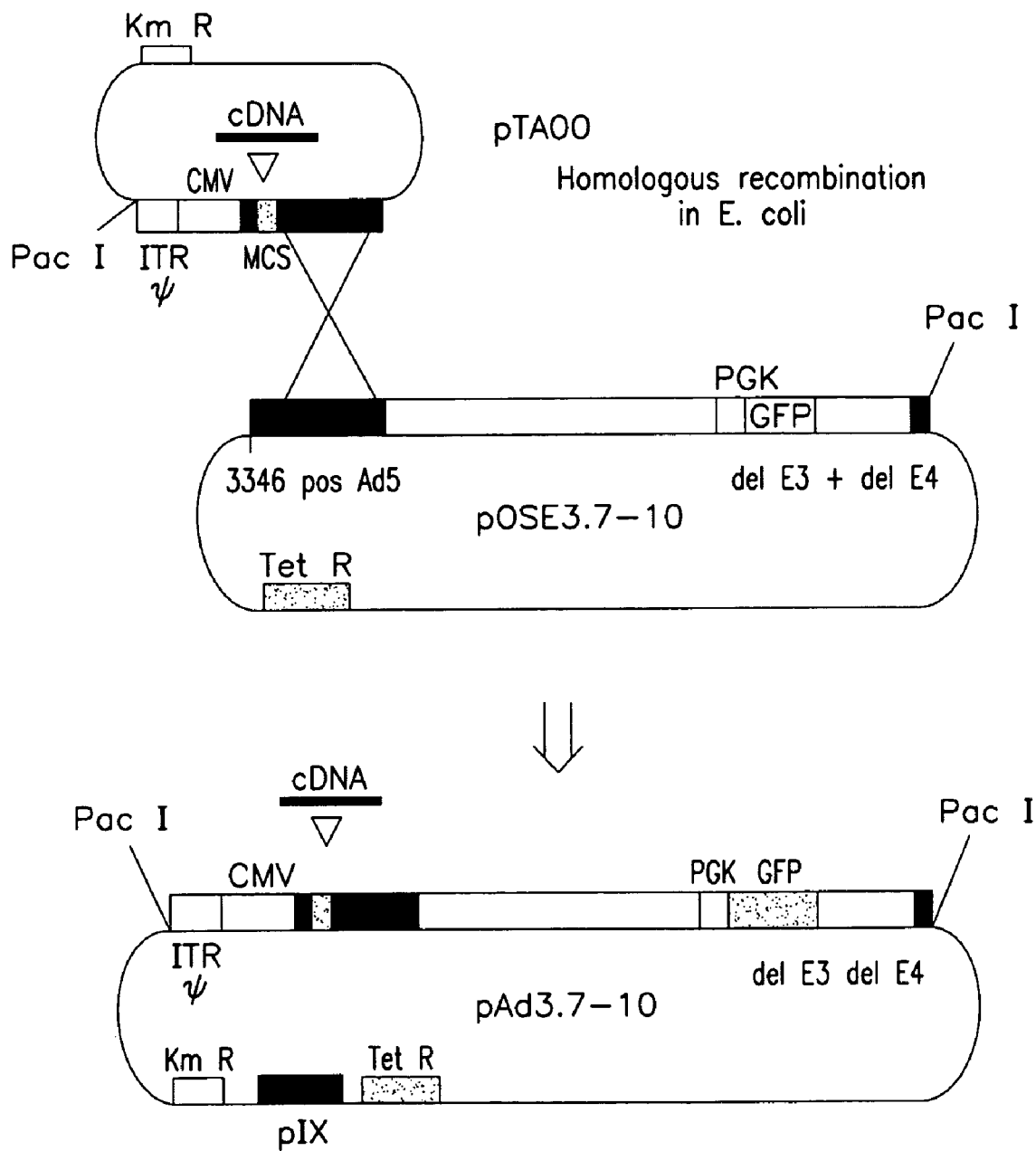
FIG. 8 Using the invention process to obtain a library of adenoviral genomes which were generated by a primary library of cDNA in the shuttle plasmid pTA00. The library of adenoviral genomes is obtained using the parental plasmid pOSE37-10, which is a plasmid which is derived from pOSE37-00. Maps of plasmids pTA00, pOSE37-10 and pAd37-10.

The series of steps is shown diagrammatically in FIG. 2, and the plasmid structures used for obtaining the adenoviral expression library are depicted in FIG. 8.

Example 5.1

Preparing the cDNA Library in the Shuttle Vector

For preparing the library in the shuttle vector (a derivative of pIG5 in which the LacZ gene was excised and replaced with multiple cloning sites, in particular XhoI and EcoRI sites), 10-20 μg of cesium gradient-purified vector are digested, at 37° C. for 90 minutes, with 5U of the enzymes XhoI and EcoRI per μg. The digest is loaded onto an agarose gel (1% Seakem GTG) and the linearized vector is separated by electrophoresis in TAE buffer. The band corresponding to the vector is cut out following visualization on a UV table. The vector is eluted from the agarose (Qiaquick DNA Cleanup System, Quiagen, Germany) and purified by means of a phenol/chloroform extraction followed by precipitation with ethanol. Following ligation of a test insert which has been digested with EcoR1 and Xho1, this vector gives rise to approximately 5 million clones/µg with a background of less than 10%.

Preparing the cDNA molecules: The cDNA is synthesized using an mRNA-enriched RNA population. The first strand is synthesized in accordance with standard protocols using Superscript II transcriptase (Stratagène) and an oligodT primer which possesses the sequence of a XhoI site in the 5' position. The second strand is synthesized using the *E. coli* DNA polymerase I enzyme in the presence of RNAse H and *E. coli* DNA ligase. The ends which are generated by the second strand are filled in by the action of T4 DNA polymerase.

The cDNA molecules are size-fractionated by gel filtration chromatography using Biogel A50M as previously described (Soares et al. PNAS, 91:9228-9232). The size-fractionated cDNA molecules are ligated to commercially available EcoRI adapters (Stratagene) and then digested with EcoRI in order to create cDNA fragments provided with (5') EcoRI and (3') XhoI ends. The unligated adapters are removed by chromatography on a Sepharose CL4B column (Pharmacia). The cDNA molecules carrying the adapters are phosphorylated using T4 polynucleotide kinase and are ligated, using T4 DNA ligase, at 16° C. and for a period of up to 48 h, into the EcoRI and XhoI sites of the shuttle vector, which has been prepared as described above (600 ng of vector +300 ng of insert in a volume of 10-20 µl). The library is amplified by electroporating it into the pir.116+ strain, which permits replication of plasmids having an RK6 origin of replication, with this strain then being spread on agar LB medium plus kanamycin in 100 dishes of 150 mm in diameter. A library of 5 million clones is obtained. The primary cDNA library in the shuttle plasmid is then standardized in accordance with the protocol described by Soares et al. 1994. A subset of clones can then be subjected to a selection step using technologies which enable the expression profile of the clones to be determined, for example using AND chips (Amersham, Molecular Dynamics, Affymetrix).

The selected clones, derived from the standardized cDNA library, in the shuttle plasmid are arranged in 96-deep well microplates at the rate of one clone per well. These clones are amplified in liquid medium (LB) in the presence of the appropriate antibiotic (kanamycin). The DNA from each clone in a batch of 96 culture samples is prepared simultaneously using a Quiagen robot (Quiagen Biorobot 9600) and the Quiaprep 96 Turbo Biorobot kit (Quiagen, Germany). The DNA samples are taken up in 50 µl of TEx1. 96 plasmid DNA samples are arranged in each so-called primary plate.

Example 5.2

Preparing the Plasmid Library of Functional Adenoviral Genomes Carrying the cDNA Molecules The parental adenoviral genome carried by an RK2 plasmid (pOSE37-00) is introduced into the JM83 strain by conventional transformation. A culture of this strain harboring the plasmid (JM83xpOSE37-00) is rendered competent by the standard techniques involving successive washes in 100 mM $CaCl_2$.

The competent cells (JM83xpOSE37-00) are distributed in a 96-deep well microplate at the rate of 40 µl per well. The DNA of each shuttle plasmid is transformed into this strain in order to obtain the homologous recombination event generating the functional adenoviral genome. 5 µl of DNA derived from the so-called primary plate are then added to the 40 µl of competent cells while adhering to the layout. The plate is brought to 42° C. for 1 min and then replaced on ice for 2 min. 1 ml of medium (LB) containing the two appropriate antibiotics (kanamycin and tetracycline) is added per well. The cells are first grown for 6 h, after which 50 µl of this first growth are used to seed a new 96-deep well plate which is provided with 1 ml of medium (LB), containing the two appropriate antibiotics (kanamycin and tetracyline), per well. Culture is then continued for 14 h.

The plasmid DNA resulting from this latter growth is purified using a Quiagen robot (Quiagen Biorobot 9600) and the R.E.A.L. Prep 96 Biorobot kit, to which is added a Quiawell separation step, derived from the Qiawell 96 Ultra Biorobot Kit, before the precipitation in isopropanol (Quiagen, Germany). The DNA is taken up in 50 µl of TEx1.

20 µl of each DNA (approximately 0.4 µg) are then transferred into a well of a new 96-well microplate while adhering to the layout. This DNA is digested with the enzyme PacI in order to excise the viral genome. 10 µl of reaction mixture (3 µl of Ne1 buffer, 6 µl of H20, 1 µl (2.5 U) of PacI) are added to 20 µl of DNA per well. The reaction is carried out at 37 C for 1 h 30. The plate is centrifuged and frozen at $-20°$ C. until used for the following step.

The viral DNA has to be digested with PacI, in order to excise the adenoviral genome, and then transfected into transcomplementing eukaryotic cells in order to generate the viral library.

Example 5.3

Obtaining the Adenoviral Expression Library

The 96-well plate carrying the PacI-digested DNA samples is brought to ambient temperature. 2 µl of Enhancer and 50 µl of Effectene (Effectene Transfection Reagent, Quiagen, Germany) are added to the 30 µl of PacI-digested DNA which is present in each well. The transfecting mixture is then distributed into the wells of a 96-well or 48-well plate or IGRP2 cells (WO96/22378) have been seeded at a rate of $10^5$ cells per $cm^2$.

Fourteen day after the transfection, 50-75 µl of culture supernatant are removed per well and used as an inoculum for infecting a new plate of freshly seeded transcomplementing cells. This amplification step is repeated 3-5 times to ensure homogeneity in the viral titers obtained in each of the wells. The titer obtained in each of the wells is between $5 \times 10^8$ and $5 \times 10^9$ viral particles per ml. The plate is centrifuged and frozen at $-20°$ C.

These viruses can be used directly on the appropriate biological system. After the cell model has been infected with the library, a functional analysis is decided upon and then implemented. More preferably, a proapoptotic, antiangiogenic or antiapoptotic activity is sought, depending on the cell model employed. The layout of the clones, and then of the viruses, during the construction of the library makes it easy to work back to the nucleotide sequence which is linked to a functional activity and thus to define a new target.

Example 6

Constructing a Plasmid which is Carrying an Adenoviral Genome and which is Compatible with the Gateway® Cloning System which is Marketed by Life Technologies (LTI, Rockeville, Mass., USA).

Figure 9:
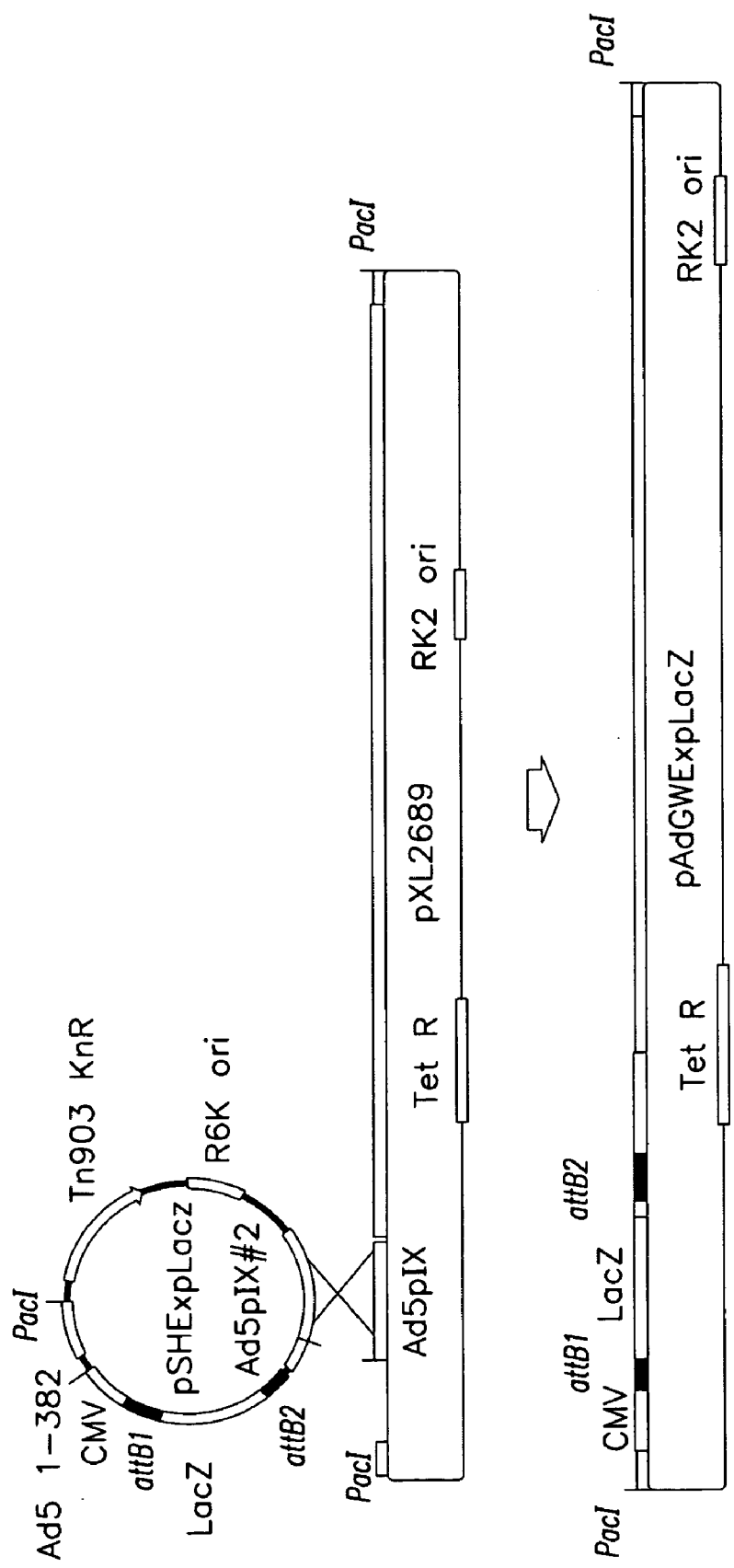
FIG. 9 Obtaining an expression plasmid, i.e. pAdGWExpLacZ, which is compatible with the Gateway® system (LTI, Rockeville, Mass., USA), by homologously recombining the plasmids pSHExpLacZ and Px12689.

The plasmid pSHExplacZ is generated; it possesses the CMV promoter, the attB1 site, the LacZ gene, the attB2 site and the SV40 polyadenylation site in a shuttle vector of the pIG5 type (FIG. 2). In order to obtain this plasmid, the cDNA corresponding to the LacZ gene, derived from the plasmid pSV40-lacZ (Promega), is digested with HindIII and DraI and inserted into the XmnI and EcoRV sites of pENTR1A, which is described by Life Technologies in (U.S. Pat. No. 5,888,732), thereby giving rise to the plasmid pENTR-LacZ. A reaction of the LR type (Gateway® cloning technology) between pENTR-LacZ and pDest12.2 gives pExpLacZ (the Gateway® technology designation). Two steps of subcloning facilitated the final isolation of pSHExpLacZ: the NcoI/AseI fragment of pExpLacZ is inserted between AseI and NcoI in pCA350 (derivative of pIG5), thereby generating the plasmid pSExpLacZ. Finally, the PacI/SalI fragment of pSExpLacZ is inserted between the PacI and SalI sites of the plasmid pIG7 (derivative of pIG5). In the end, the sequences: CMV promoter, attB1 site, LacZ gene, attB2 site and SV40 polyadenylation site are located, in place of the CMV-LacZ cassette, in the shuttle plasmid pIG5 (Example 2). The plasmid which is thus obtained is designated pSHExpLacZ and is depicted in FIG. 9.

A plasmid designated pAdGWExpLacZ, which is compatible with the Gateway® system, is then constructed in accordance with the EDRAG methodology (FR 2,730,504) and using the plasmids pSHExpLacZ and pXL2689.

The plasmid pXL2689, which is described by Crouzet et al. (*PNAS* 1997), possesses the origin of the plasmid RK2, the gene for resistance to tetracycline and an infectious adenoviral genome possessing deletions in E1 and E3. Recombination of the plasmids pXL2689 and pSHExpLacZ gives rise to the plasmid pAdGWExpLacZ, which carries the adenoviral genome and the insert comprising the CMV promoter, the attB1 site, the LacZ gene, the attB2 site and the SV40 polyadenylation site (FIG. 9).

Figure 10:
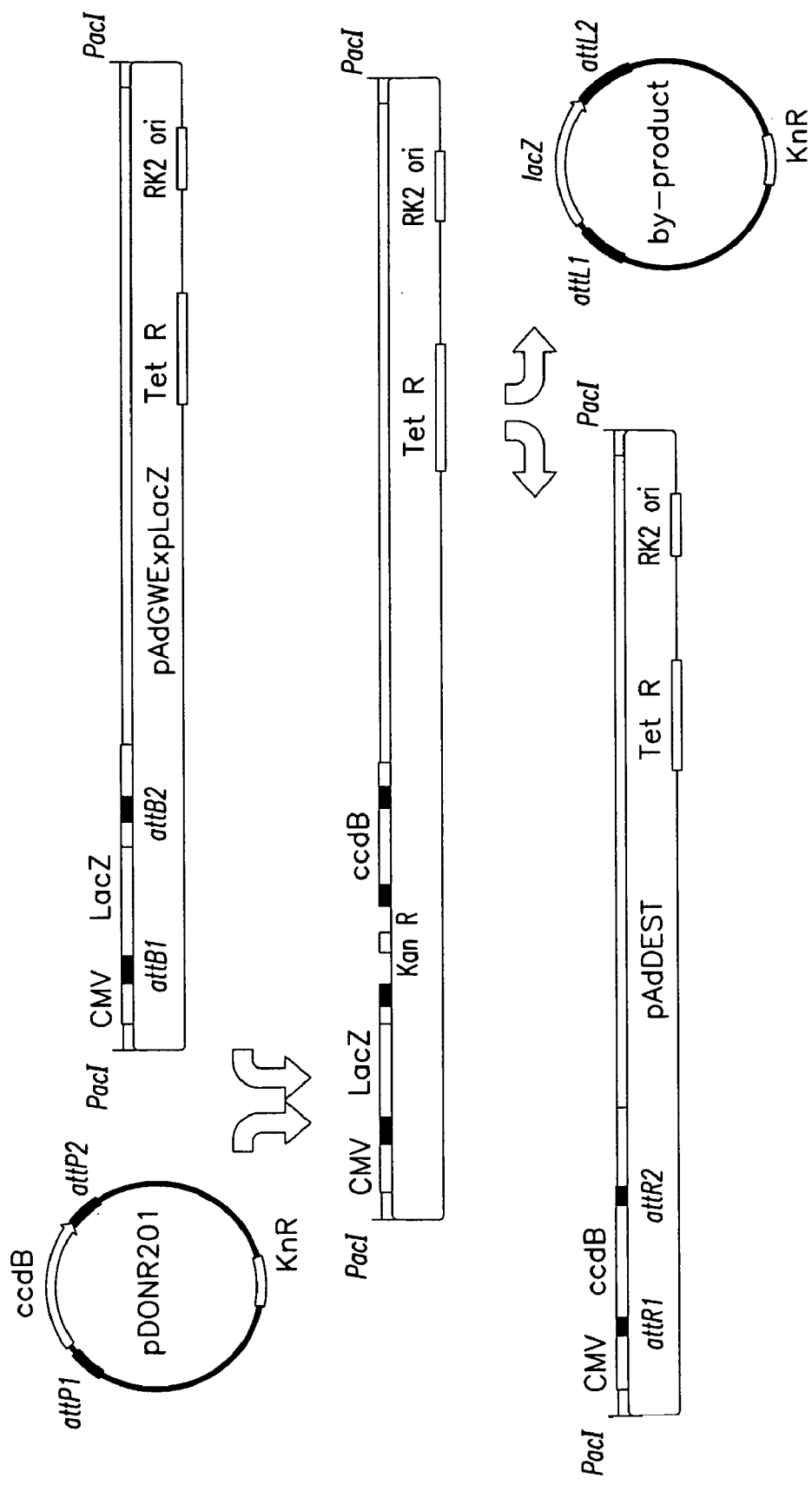
FIG. 10 Using what is termed a BP reaction to obtain a Destination plasmid, i.e. pAdDEST, which carries a complete adenoviral genome, with the gene ccdB, which is lethal for *E. Coli*, being surrounded by the recombination sites attR1 and attR2.

The plasmid pAdGWExpLacZ, which is thus obtained, comprises a gene of interest, represented by LacZ, between the two attB recombination sites of the *E. Coli* phage lambda and reacts with a donor vector of the Gateway® system (pDONR201), which carries the attP sites, a gene for resistance to kanamycin ($Kn^R$) and the gene ccdB, which is lethal for *E. Coli*. The plasmid which results from this reaction, which is termed a BP reaction in accordance with the terminology used in the Gateway® cloning technology, is designated pAdDEST (Destination plasmid) and is depicted in FIG. 10.

Figure 11:
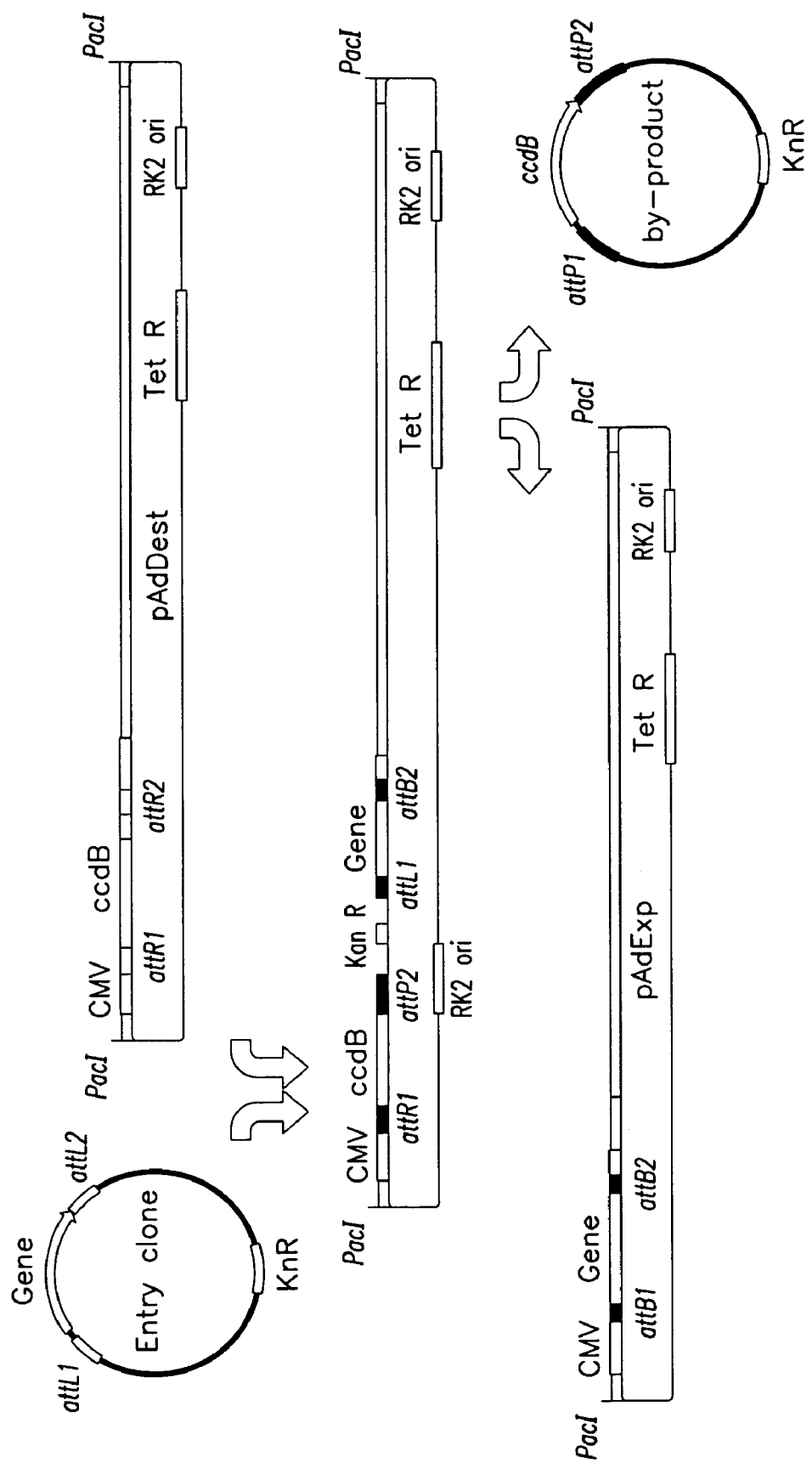
FIG. 11 Obtaining the adenoviral plasmid pAdExp, which carries an insert of interest, by means of what is termed an LR reaction.

Finally, owing to the attR1 and attR2 sites, the plasmid pAdDEST reacts with an Entry clone of the Gateway® system, which clone carries an insert of interest surrounded by the attL1 and attL2 recombination sites, by means of what is termed an LR reaction. The resulting plasmid is designated pAdExp and carries a complete adenoviral genome as well as the insert of interest (FIG. 11).

REFERENCES

Ausubel et al., 1987. Current protocols in molecular biology 1987-1988. John Willey and Sons, New York.
Bolivar et al., 1977. Gene 2:95.
Crouzet et al., 1997, PNAS 94, 1414-1419
Dagert et al., 1979. Gene, 6, 23-28.
Ditta et al., 1980. Plasmid, 13, 149-154.
Ghosh-Choudhurry et al. 1986. Gene, 50, 161-171.
Hamilton et al., 1989. J. Bacteriol. 171:4617-4622.
Hanahan, D. 1983. J. Mol. Biol. 166:557.
Heffron et al., 1977. Proc. Natl. Acad. Sci. USA, 74, 702-706.
Maniatis T., et al. 1982. Molecular Cloning: A Laboratory Manual, Cold Spring Harbor Laboratory, New York.
Miller, et al., 1988. J. Bacteriol. 170:2575-2583.
Simoes, et al. 1991. New York Acad. Sci. 646:254-258.
Sinha N. D. et al. 1984. Nucl. Acids Res., 12, 4539-4557.
Slater, et al. 1993. J. Bacteriol. 175:4260-4262.
Viera, et al., 1982. Gene, 19, 259-268.
Wirth, et al. 1989. Mol. Gen. Genet., 216, 175-177.
Zeef, et al. 1994. EMBO J. 13:5113-5120.

The invention claimed is:

1. A method for producing adenoviruses, which comprises:
    a) constructing a shuttle plasmid, which comprises a first truncated recombinant adenoviral genome which contains at least one heterologous nucleic acid,
    b) bringing this shuttle plasmid into contact with a parent plasmid, which comprises a second truncated recombinant adenoviral genome which is complementary to the first genome, making it possible, by means of one homologous recombination step, to produce a final plasmid which comprises a complete recombinant adenoviral genome, and
    c) excising the complete linear recombinant adenoviral genome from the final plasmid and introducing it into an encapsidating cell line in order to produce the recombinant adenoviruses which incorporate the complete recombinant adenoviral genome,
    said shuttle plasmid and parent plasmid both comprising an ITR sequence bordered by a restriction site not present on the adenoviral genome.

2. The method according to claim 1, which additionally comprises using the recombinant adenoviruses which have been produced to infect: (i) a biological material comprising cells, for the purpose of analyzing the properties of the nucleic acid; (ii) a cell culture in vitro or ex vivo, for the purpose of producing a protein, polypeptide or peptide which is encoded by the heterologous nucleic acid; or (iii) a cell, tissue, organ or organism, for the purpose of producing in vivo a protein, polypeptide or peptide which is encoded by the heterologous nucleic acid.

3. The method according to claim 1 or 2, characterized in that in step a), the first truncated genome comprises an ITR, a heterologous nucleic acid, a region of adenoviral homology and, an encapsidation sequence.

4. The method according to claim 1 or 2, characterized in that, in step a), the second truncated adenoviral genome comprises at least one ITR, a region of adenoviral homology which is identical to that present in the first truncated adenoviral genome, and an encapsidation sequence if the latter is not present in the first truncated adenoviral genome.

5. The method according to claim 1, wherein the produced adenovirus is used for producing adenoviral expression libraries.

6. A kit which comprises: a shuttle plasmid comprising a first truncated adenovirus genome, and a second parent plasmid comprising a second truncated adenovirus genome, with the two plasmids being able to produce, by means of one homologous recombination step between the two truncated adenovirus genomes, a final plasmid which comprises a complete linear recombinant adenovirus genome which is flanked by one or more restriction sites which is/are not present in said genome, said shuttle plasmid and parent plasmid both comprising an ITR sequence bordered by a restriction site not present on the adenoviral genome.

7. The method of claim 1, wherein the shuttle plasmid is a prokaryotic plasmid.

8. A method for producing adenoviruses, which comprises:
    a) constructing a shuttle plasmid, which comprises a first truncated recombinant adenoviral genome which contains at least one heterologous nucleic acid, b) bringing this shuttle plasmid into contact with a parent plasmid, which comprises a second truncated recombinant adenoviral genome which is complementary to the first genome, making it possible, by means of one homologous recombination step, to produce a final plasmid which comprises a complete recombinant adenoviral genome, and c) excising the complete linear recombinant adenoviral genome from the final plasmid and introducing it into an encapsidating cell line in order to produce the recombinant adenoviruses which incorporate the complete recombinant adenoviral genome, said shuttle plasmid and said parent plasmid both comprising an identical adenoviral homology region, both comprising an origin of replication and a different selection marker for selecting each element and both comprising an ITR sequence bordered by a restriction site not present on the adenoviral genome, and one or other comprising an encapsidation sequence.

9. The method according to claim 8, which additionally comprises using the recombinant adenoviruses which have been produced to infect: (i) a biological material comprising cells, for the purpose of analyzing the properties of the nucleic acid; (ii) a cell culture in vitro or ex vivo, for the purpose of producing a protein, polypeptide or peptide which is encoded by the heterologous nucleic acid, a cell; or (iii) a tissue, organ or organism, for the purpose of producing in vivo a protein, polypeptide or peptide which is encoded by the heterologous nucleic acid.

10. The method according to claim 8 or 9, wherein the produced adenovirus is used for producing adenoviral expression libraries.

11. The method of claim 8, wherein the shuttle plasmid is a prokaryotic plasmid.

12. A kit which comprises: a shuttle plasmid comprising a first truncated adenovirus genome, and a parent plasmid comprising a second truncated adenovirus genome, with the two plasmids being able to produce, by means of one homologous recombination step between the two truncated adenovirus genomes, a final plasmid which comprises a complete linear recombinant adenovirus genome which is flanked by one or more restriction sites which is/are not present in said genome, said shuttle plasmid and said parent plasmid both comprising an identical adenoviral homology region, both comprising an origin of replication and a different selection marker for selecting each element and both comprising an ITR sequence bordered by a restriction site not present on the adenoviral genome, and one or other comprising an encapsidation sequence.

13. The kit according to claim 6, wherein the second truncated adenoviral genome comprises at least one ITR, a region of adenoviral homology which is identical to that present in the first truncated adenoviral genome, and an encapsidation sequence if the latter is not present in the first truncated adenoviral genome.

14. The kit according to claim 6 or 13, wherein the produced adenovirus is used for producing adenoviral expression libraries.

15. The kit according to claim 6 or 13, wherein the shuttle plasmid is a prokaryotic plasmid.

16. The kit according to claim 12, wherein the produced adenovirus is used for producing adenoviral expression libraries.

17. The kit according to claim 12, wherein the shuttle plasmid is a prokaryotic plasmid.

\* \* \* \* \*